(12) United States Patent
Gunderson et al.

(10) Patent No.: US 7,289,851 B2
(45) Date of Patent: Oct. 30, 2007

(54) METHOD AND APPARATUS FOR IDENTIFYING LEAD-RELATED CONDITIONS USING IMPEDANCE TRENDS AND OVERSENSING CRITERIA

(75) Inventors: Bruce D. Gunderson, Plymouth, MN (US); Amisha S. Patel, Maple Grove, MN (US); Chad A. Bounds, St. Paul, MN (US); Li Wang, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 375 days.

(21) Appl. No.: 10/818,098

(22) Filed: Apr. 5, 2004

(65) Prior Publication Data

US 2005/0137636 A1 Jun. 23, 2005

Related U.S. Application Data

(60) Provisional application No. 60/526,915, filed on Dec. 4, 2003.

(51) Int. Cl.
*A61N 1/08* (2006.01)
(52) U.S. Cl. .................................. 607/27
(58) Field of Classification Search ............ 607/27, 607/28
See application file for complete search history.

(56) References Cited

U.S. PATENT DOCUMENTS

| | | | |
|---|---|---|---|
| 4,825,869 A | 5/1989 | Sasmor et al. ......... 128/419 PT | |
| 5,003,975 A | 4/1991 | Hafelfinger et al. | |
| 5,117,824 A | 6/1992 | Keimel et al. | |
| 5,215,081 A | 6/1993 | Ostroff | |
| 5,741,311 A | 4/1998 | McVenes et al. | |
| 5,755,742 A | 5/1998 | Schuelke et al. | |
| 5,776,168 A | 7/1998 | Gunderson ........... 607/27 | |
| 5,897,577 A | 4/1999 | Cinbis et al. | |
| 5,910,156 A | 6/1999 | Cinbis et al. ........... 607/27 | |
| 6,067,473 A | 5/2000 | Greeninger et al. | |
| 6,129,746 A | 10/2000 | Levine et al. | |
| 6,317,633 B1* | 11/2001 | Jorgenson et al. ....... 607/28 |
| 6,493,586 B1* | 12/2002 | Stahmann et al. ....... 607/27 |
| 6,629,931 B1* | 10/2003 | Begemann et al. ...... 600/508 |
| 6,658,294 B1* | 12/2003 | Zadeh et al. ........... 607/28 |
| 6,721,600 B2* | 4/2004 | Jorgenson et al. ....... 607/27 |
| 2001/0031997 A1 | 10/2001 | Lee | |
| 2001/0037366 A1 | 11/2001 | Webb et al. | |
| 2002/0116031 A1* | 8/2002 | Vonk ................. 607/28 |
| 2002/0120307 A1 | 8/2002 | Jorgenson et al. | |
| 2004/0015197 A1* | 1/2004 | Gunderson ........... 607/27 |
| 2004/0230242 A1* | 11/2004 | van Dam et al. ....... 607/27 |
| 2005/0137636 A1* | 6/2005 | Gunderson et al. ...... 607/27 |
| 2005/0159785 A1* | 7/2005 | Rueter ................ 607/28 |

FOREIGN PATENT DOCUMENTS

WO WO 03/077822 A2 9/2003

* cited by examiner

*Primary Examiner*—George Manuel
*Assistant Examiner*—Christopher A. Flory
(74) *Attorney, Agent, or Firm*—Michael C. Soldner

(57) ABSTRACT

A method and apparatus for detecting a lead-related condition that includes determining whether a first oversensing criteria is satisfied, determining whether a second oversensing criteria is satisfied, determining whether an impedance criteria has been satisfied, and generating an alert in response to more than one of the first oversensing criteria, the second over sensing criteria and the impedance criteria being satisfied.

11 Claims, 16 Drawing Sheets

METHOD AND APPARATUS FOR IDENTIFYING LEAD-RELATED CONDITIONS USING IMPEDANCE TRENDS AND OVERSENSING CRITERIA

RELATED APPLICATION

The present application claims priority and other benefits from U.S. Provisional Patent Application Ser. No. 60/526,915, filed Dec. 4, 2003, entitled "METHOD AND APPARATUS FOR IDENTIFYING LEAD-RELATED CONDITIONS USING IMPEDANCE TRENDS AND OVERSENSING CRITERIA", incorporated herein by reference in its entirety.

FIELD OF THE INVENTION

The present invention relates generally to implantable medical devices, and in particular to a method for automatically identifying lead-related conditions based on lead impedance measurement trends and oversensing parameters.

BACKGROUND OF THE INVENTION

A wide variety of implantable medical devices for delivering a therapy or monitoring a physiologic condition which may employ one or more elongated electrical leads and/or sensors have been clinically implanted or proposed for clinical implantation in patients. Such implantable medical devices may deliver therapy or monitor the heart, muscle, nerve, brain, stomach or other organs. Implantable medical devices such as pacemakers and implantable cardioverter defibrillators (ICDs), are available for arresting cardiac arrhythmias by delivering electrical impulses to the heart. Such devices sense the heart's intrinsic rhythm through cardiac leads carrying electrodes that may be implanted in the heart. When an abnormal rhythm is detected, which may be bradycardia, tachycardia or fibrillation, an appropriate electrical therapy is delivered to restore the heart's normal rhythm.

Leads associated with such implantable medical devices typically include a lead body extending between a proximal lead end and a distal lead end and incorporates one or more exposed electrode or sensor elements located at or near the distal lead end. One or more elongated electrical conductors extend through the lead body from a connector assembly provided at a proximal lead end for connection with an associated implantable medical device and an electrode located at the distal lead end or along a section of the lead body. Each electrical conductor is typically electrically isolated from any other electrical conductors and is encased within an outer sheath that electrically insulates the lead conductors from body tissue and fluids.

Implantable medical device leads may extend from a subcutaneous implantation site of the implantable medical device through an internal body pathway to a desired tissue site. The leads are generally preferred having small diameter, highly flexible, reliable lead bodies that withstand degradation by body fluids and body movements that apply stress and strain to the lead body and the connections made to electrodes. As lead bodies are made smaller and smaller and the number of lead conductors is increased or maintained, problems with lead insulation and integrity of lead conductors may become more prevalent.

Cardiac lead bodies are continuously flexed by the beating of the heart. Other stresses are applied to the lead body during an implantation or lead repositioning procedure. Movements by the patient can cause the route traversed by the lead body to be constricted or otherwise altered causing stresses on the lead body. At times, the lead can be slightly damaged during surgical implantation, and the slight damage may progress in the body environment until a lead conductor fractures and/or the insulation is breached. The effects of lead body damage may progress from an intermittent manifestation to a more continuous lead related condition. In extreme cases, insulation of one or more of the electrical conductors may be breached, causing the conductors to contact one another or with body fluids resulting in a low impedance or short circuit. In other cases, a lead conductor may fracture and exhibit an intermittent or continuous open circuit resulting in an intermittent or continuous high impedance.

Other problems can arise at the proximal lead end where the electrical connection between implantable medical device connector elements and the lead connector elements may be intermittently or continuously disrupted, resulting in a high impedance or open circuit. Usually, such connector open circuit problems result from insufficient tightening of connection mechanisms, such as a set screw, at the time of implantation followed by a gradual loosening of the connection until contact becomes intermittent or open or an incomplete lead pin insertion.

Such lead problems resulting in short or open circuits may be referred to, for simplicity, as "lead related conditions." Typically, it is necessary for an attending clinician to diagnose the nature of a lead-related condition from available data, test routines, and patient symptoms. Then, it is necessary for the clinician to take corrective action, e.g., to either replace the lead, select different electrodes for sensing or pacing, or tighten the proximal connection. In severe cases, the lead-related condition may result in premature depletion of the battery energy of the implantable medical device, requiring its replacement.

In the case of cardiac leads, the ability to sense an intrinsic heart rhythm accurately through a lead can be impaired by any of the above described lead related conditions. Complete lead breakage impedes any sensing functions, lead conductor fractures or intermittent contact can cause electrical noise that interferes with accurate sensing. Oversensing or undersensing can occur resulting in an incorrect interpretation of the heart rhythm by a pacemaker or ICD, potentially resulting in inappropriate withholding or delivery of electrical therapy. For example, oversensing may lead to the detection of tachycardia or fibrillation resulting in the inappropriate delivery of a high voltage shock therapy. Such therapy is painful to the patient and may be experienced repeatedly if a lead related condition is not diagnosed and corrected. Such inappropriate therapies deplete the ICD battery energy prematurely and could inappropriately induce ventricular fibrillation if delivered onto the T-wave.

During cardiac pacing or defibrillation, increased impedance of the stimulation path or the short circuit of lead conductors due to one of the above-described lead related conditions can reduce the effectiveness of a pacing or shocking below that sufficient to pace or defibrillate the heart.

The failure of the delivered therapy can be dangerous to the patient and/or can necessitate applying further, higher energy, pacing or cardioversion/defibrillation shocks, which can increase discomfort to the patient and is wasteful of battery energy.

Certain pacemakers and ICDs have been provided with the capability of storing cardiac electrogram data prompted by the automatic determination of oversensing or undersensing of cardiac events, loss of effective pacing, out of range lead impedance measurements, etc. Such data can be telemetered to an external programmer when the physician interrogates the implantable medical device and used by the clinician in troubleshooting any problems.

The lead impedance data and other parameter data is typically compiled and displayed on a monitor and/or printed out for analysis by the clinician. The clinician may undertake real time IPG parameter reprogramming and testing and observe the monitored surface ECG to try to pinpoint a suspected lead related condition that is indicated by the data and/or patient and/or device symptoms.

The diagnosis of lead related data at a later time is useful, but it is believed preferable to provide a more immediate response to a lead related condition by the IPG or monitor. The retrieved data may be suspect if a lead related condition causes the stored or real time telemetered data to be inaccurate. The physician may mistakenly rely upon such data to maintain or change programmed pacing parameters and modes, particularly if a lead related condition is intermittent and is not diagnosed.

Many proposals have been advanced to determine if a lead related condition has occurred and to modify the IPG operation and/or to provide a warning that is perceptible by the patient or can be telemetered to the external programmer when the physician interrogates the IPG or monitor. In addition, it has been a goal to automatically detect a lead conductor related condition and respond by switching pacing pathways to use available lead conductors that appear to be functioning properly.

Comparison of a lead impedance measurement taken at a particular point in time to a fixed range of acceptable values or a fixed reference value, such as disclosed for example in U.S. Pat. No. 6,317,633, issued to Jorgenson et al., incorporated herein by reference in its entirety, can be useful in detecting a lead-related condition that has already manifested itself as an extremely high or extremely low impedance. Setting a fixed range, however, does not allow gradually occurring lead conditions to be detected early on. Defining a fixed range more narrowly in order to detect a lead condition earlier may result in undesired false positive detections causing a clinician to spend time investigating a problem that may not exist. A lead-related condition that is gradually worsening over time may still affect lead and IMD performance. Such conditions are preferably caught early to prevent clinical manifestation of the problem. Therefore, it is desirable to monitor trends of lead impedance changes so that a gradually occurring condition may be detected early on. Furthermore, recognition of the time course of the development of a lead-related condition may be important in diagnosing the cause and allowing prompt, appropriate corrective action.

Specific types of lead-related conditions may be associated with certain types of lead designs. For example, degradation of insulation between conductors may be specific to certain types of leads having coiled conductors arranged coaxially within the lead body, isolated from each other by an intervening insulating layer. After chronic exposure to the considerably hostile environment within the human body, the middle layers of insulation may break down between the conductors within the lead body. Metal ionized oxidation of the middle layers is thought to be the mechanism behind this type of middle insulation degradation, which allows the infiltration of body fluids to create a short between two conductors running coaxially. The gradual degradation of the middle insulating layer results in a gradual decrease in sub-threshold impedance measured between the two electrodes associated with the two shorted conductors. This phenomenon has been observed between the ring electrode conductor and the coil electrode conductor in true bipolar cardiac defibrillation leads. Because the ring electrode is generally used for sensing the heart's intrinsic rhythm, a short between the ring electrode conductor and the coil conductor may produce oversensing and result in inappropriate therapy deliveries. While measurement of the impedance between the ring and coil electrodes show a decline, this decreased impedance could also be the result of an outer insulation breach.

Since problems associated with lead-related conditions may be intermittent and are not routinely encountered in all patients, the task of recognizing and trouble-shooting lead-related conditions can be challenging to the physician.

BRIEF DESCRIPTION OF THE DRAWINGS

Various aspects and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

The methods included in the present invention may be used in conjunction with, or incorporated in, an implantable cardiac stimulation device such as a pacemaker or an ICD, or other devices requiring a lead for stimulating excitable tissue. Preferably, methods included in the present invention are fully implemented in an implanted device. Alternatively, methods included in the present invention for analyzing oversensing measures and impedance trends that have been stored by an implantable device may be implemented in an external device capable of receiving stored impedance data through uplinking telemetry.

Figure 1:
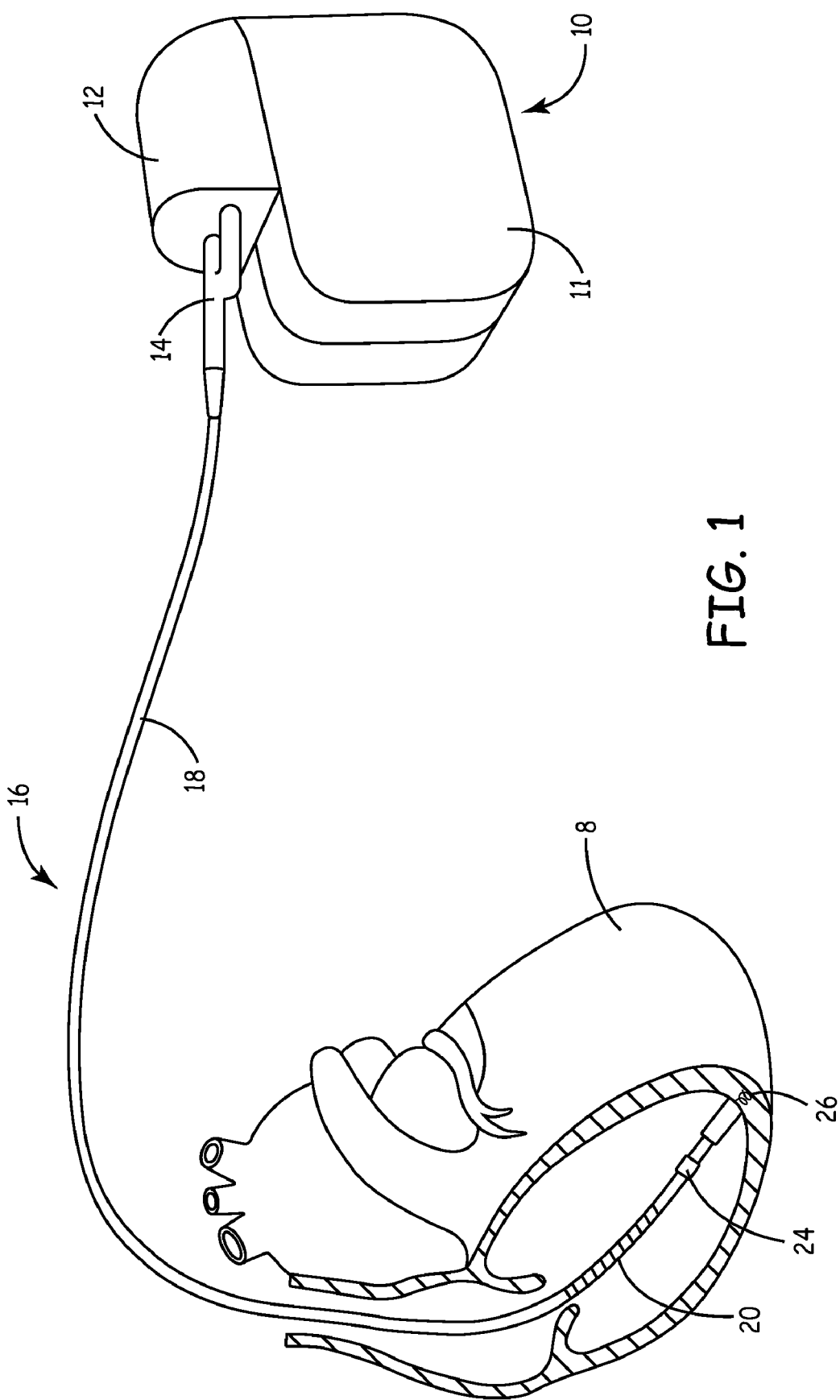
FIG. 1 is a schematic diagram of an exemplary implantable medical device in which the present invention may be usefully practiced.

An exemplary implantable medical device in the form of an implantable cardioverter defibrillator (ICD) 10 is shown in FIG. 1, with which methods included in the present invention may be used. The ICD 10 is shown coupled to a patient's heart by way of a right ventricular lead 16. A connector block 12 receives a bifurcated connector 14 at the proximal end of lead 16 for providing electrical connection to the ICD 10. Lead 16 is positioned such that its distal end is in the right ventricle for sensing right ventricular cardiac signals and delivering pacing or shocking pulses in the right ventricle. For these purposes, lead 16 is equipped with a ring electrode 24, a tip electrode 26, and a coil electrode 20, each of which are connected to an insulated conductor within the body of lead 16. The proximal end of the insulated conductors are coupled to corresponding connectors carried by bifurcated connector 14.

Electrodes 24 and 26 may be used as a bipolar pair, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with defibrillation coil electrode 20 for defibrillation of the heart. It is recognized that alternate lead configurations may be substituted for the right ventricular lead illustrated in FIG. 1.

While a particular single-chamber ICD and lead system is illustrated in FIG. 1, it is understood that methodologies included in the present invention may be adapted for use with any single chamber device and may be expanded for use with dual chamber, or multichamber ICD or pacemaker systems including multiple leads each carrying one or more electrodes. The methodologies included in the present invention may alternatively be used in other types of electrical pulse generator systems that require implantable leads for stimulating or sensing excitable body tissue.

Figure 2:
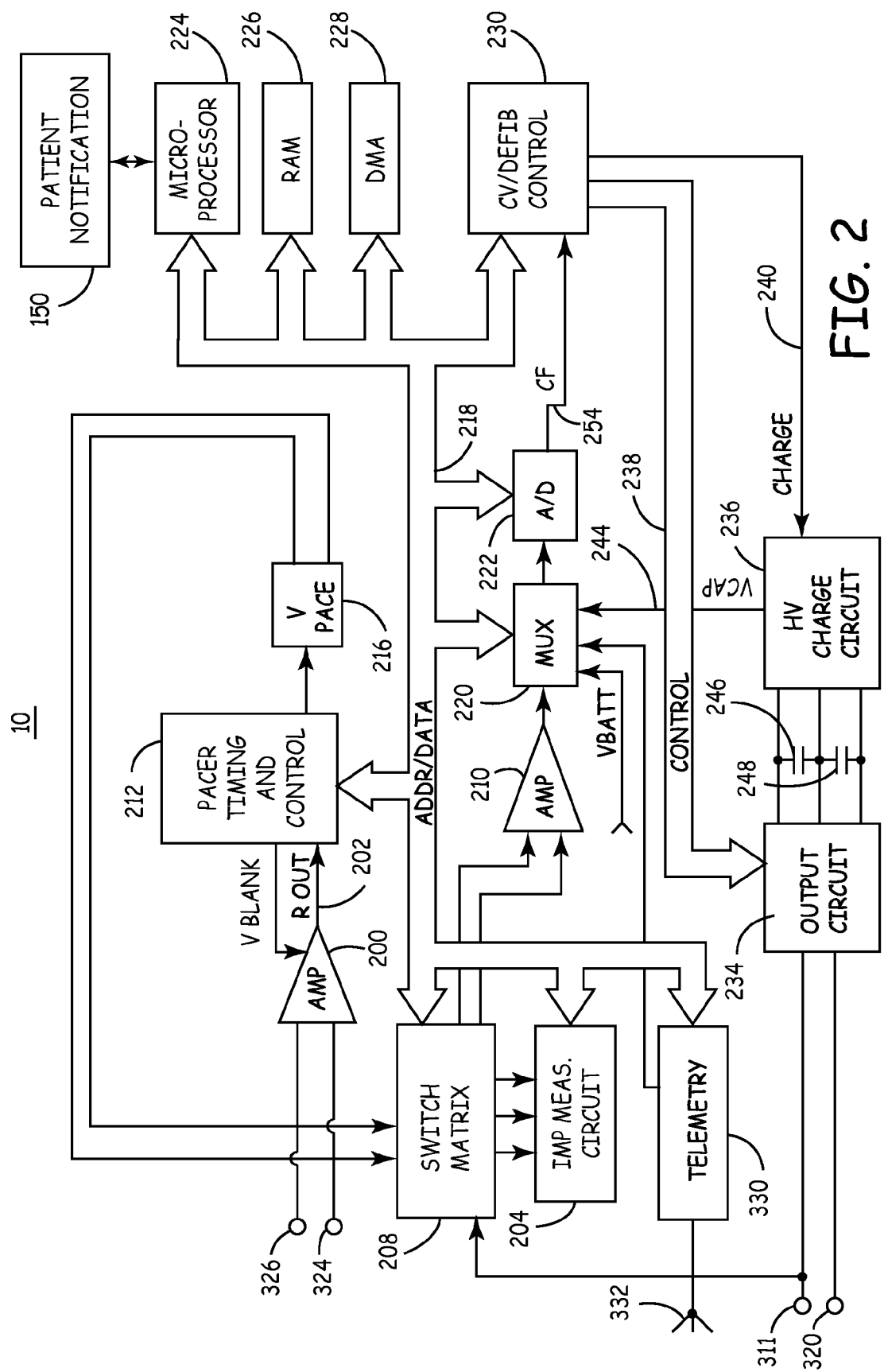
FIG. 2 is a functional, block diagram of the implantable medical device of FIG. 1, in which methods included in the present invention may be implemented.

A functional schematic diagram of ICD 10 of FIG. 1 is shown in FIG. 2. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, the ICD 10 is provided with a number of connection terminals for achieving electrical connection to the electrodes of lead 16. The connection terminal 311 provides electrical connection to the housing 11, also referred to herein as "can," for use as the indifferent electrode during unipolar stimulation or sensing. The connection terminal 320 provides electrical connection to defibrillation coil electrode 20 and is coupled to a high voltage output circuit 234 to facilitate the delivery of high energy shocking pulses to the heart using coil electrode 20 and housing 11.

The connection terminals 326 and 324 provide electrical connection to tip electrode 26 and the ring electrode 24 positioned in the right ventricle. The connection terminals 326 and 324 are further coupled to a ventricular sense amplifier 200 for sensing ventricular signals.

The ventricular sense amplifier 200 preferably takes the form of automatic gain controlled amplifier with adjustable sensing threshold. The general operation of the ventricular sense amplifier 200 may correspond to that disclosed in U.S. Pat. No. 5,117,824, by Keimel, et al., incorporated herein by reference in its entirety. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known in the art for use in implantable devices may be used.

ICD 10 includes an impedance measurement circuit 204 for performing lead impedance measurements under the control of microprocessor 224. Impedance measurements are preferably performed on a predetermined periodic basis, which may be daily or more or less frequently. Measurements may be performed at a particular time of day, such as during the night when the patient is at rest. The frequency by which impedance measurements are made may be fixed but is preferably programmable such that if a lead-related condition is suspected, impedance measurements may be selectively performed more frequently for diagnosing the lead condition. The frequency of lead impedance measurements may alternatively be adjusted automatically based on the variation between successive measurements as generally described in U.S. Pat. No. 6,129,746 issued to Levine, et al., incorporated herein by reference in its entirety. Impedance measurements may additionally be performed following a manually entered command received by telemetry circuit 330 from an external programmer. Impedance measurements may additionally be performed upon an event trigger, such as a failed pacing pulse detected as a loss of capture, due to a predetermined event, such as, for example, a non-physiologic RR interval of 120 ms. Automatic lead impedance measurement initiated by the occurrence of predetermined events is disclosed in U.S. Pat. No. 5,003,975 to Hafelfinger, et al., incorporated herein in its entirety.

Depending on the type of lead and electrodes present, both high voltage and low voltage lead impedance measurements may be performed. Impedance measurement circuit 204 selects electrodes across which an impedance is to be measured via switch matrix 208. Measured impedances may be stored in a designated area of RAM 226 with a corresponding time and date label.

In the configuration shown in FIG. 1, a low voltage impedance may be measured between tip electrode 26 and ring electrode 24 to determine a pacing impedance. An exemplary pacing impedance measurement may be performed by delivering a 120 mV, 60 μs pulse applied to the tip electrode 26 60 ms after a ventricular pacing pulse or sensed R-wave and measuring the resulting current at the ring electrode 24. A high voltage impedance measurement may be performed by delivering a 400 mV, 60 μs pulse which may be applied between the coil electrode 20 and ring electrode 24, coil electrode 20 and can 11, the ring electrode 24 and can 11, and the tip electrode 24 and coil electrode 20 to evaluate various possible conduction pathways that have a changed impedance if a conductor fractures or its insulation fails.

Impedance measurements may alternatively be performed according to methods known in the art. Examples of impedance measurement techniques are disclosed in U.S. Pat. No. 5,755,742 to Schuelke et al., U.S. Pat. No. 6,129,746 to Levine, et al., U.S. Pat. No. 5,741,311 to McVenes et al., U.S. Pat. No. 5,897,577 to Cinbis et al., U.S. Pat. No. 6,242,585 issued to Prutchi et al., and U.S. Pat. No. 5,215,081 to Ostroff, all of which patents are incorporated herein by reference in their entirety.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various pacing modes or anti-tachycardia pacing therapies. Pacer circuitry 212 also determines the amplitude of the cardiac pacing pulses under the control of microprocessor 224.

During pacing, escape interval counters within pacer timing and control circuitry 212 are reset upon sensing of R-waves as indicated by signals on line 202. In accordance with the selected mode of pacing, pacing pulses are generated by ventricular pacer output circuit 216. The pacer output circuit 216 is coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals for detecting the occurrence of a variety of arrhythmias.

The microprocessor 224 includes associated ROM in which stored programs controlling the operation of the microprocessor 224 reside. A portion of the random access memory 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, ICD 10 is preferably equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
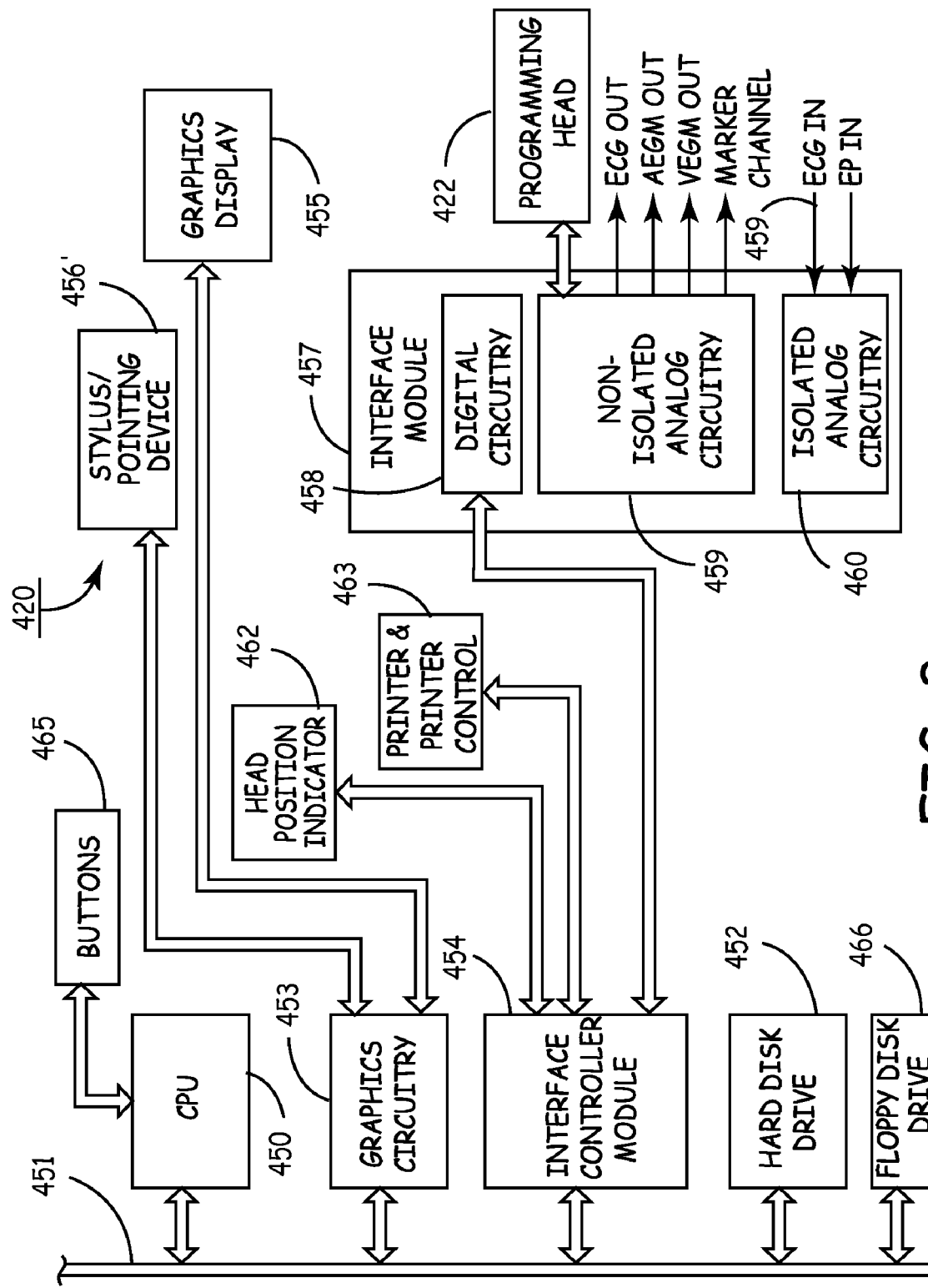
FIG. 3 is a plan view of an external programmer of a sort appropriate for use in conjunction with the practice of the present invention in an implantable medical device.

FIG. 3 is a plan view of an external programmer of a sort appropriate for use in conjunction with the practice of the present invention in an implantable medical device. The programmer 420 is a microprocessor controlled device which is provided with a programming head 422 for communicating with an implanted device, a set of surface electrogram electrodes 459 for monitoring a patient's electrogram, a display 455 which is preferably a touch sensitive display, control buttons or keys 465, and a stylus 456 for use in conjunction with the touch sensitive screen 455. By means of the control keys 465 and the touch sensitive screen 455 and stylus 456, the physician may format commands for transmission to the implantable device. By means of the screen 455, the physician may observe information telemetered from the implantable device, including diagnostic information such as sessions that were initiated, the time that they were initiated, and whether they terminated upon normal completion of the session or prior to completion of the session in response to a termination event, as described below.

The programmer is further provided with a printer 463 which allows for hard copy records of displays of signals received from the implantable device such as electrograms, stored parameters, programmed parameters, and information as to heart rate variability and heart rate trends and other diagnostic information. While not visible in this view, the device may also be provided with a floppy disk or CD ROM drive and/or a port for insertion of expansion cards such as P-ROM cartridges, to allow for software upgrades and modifications to the programmer 420.

In the context of the present invention, programmer 420 may serve simply as an output device for transmitting information to the implantable medical device, a display device, displaying information with regard to lead impedance measurements and oversensing criteria generated by the implanted device, or as an input device receiving uplinked data related to lead impedance and oversensing criteria and calculating lead-related conditions based on the information input from the implantable medical device according to the present invention.

Figure 4:
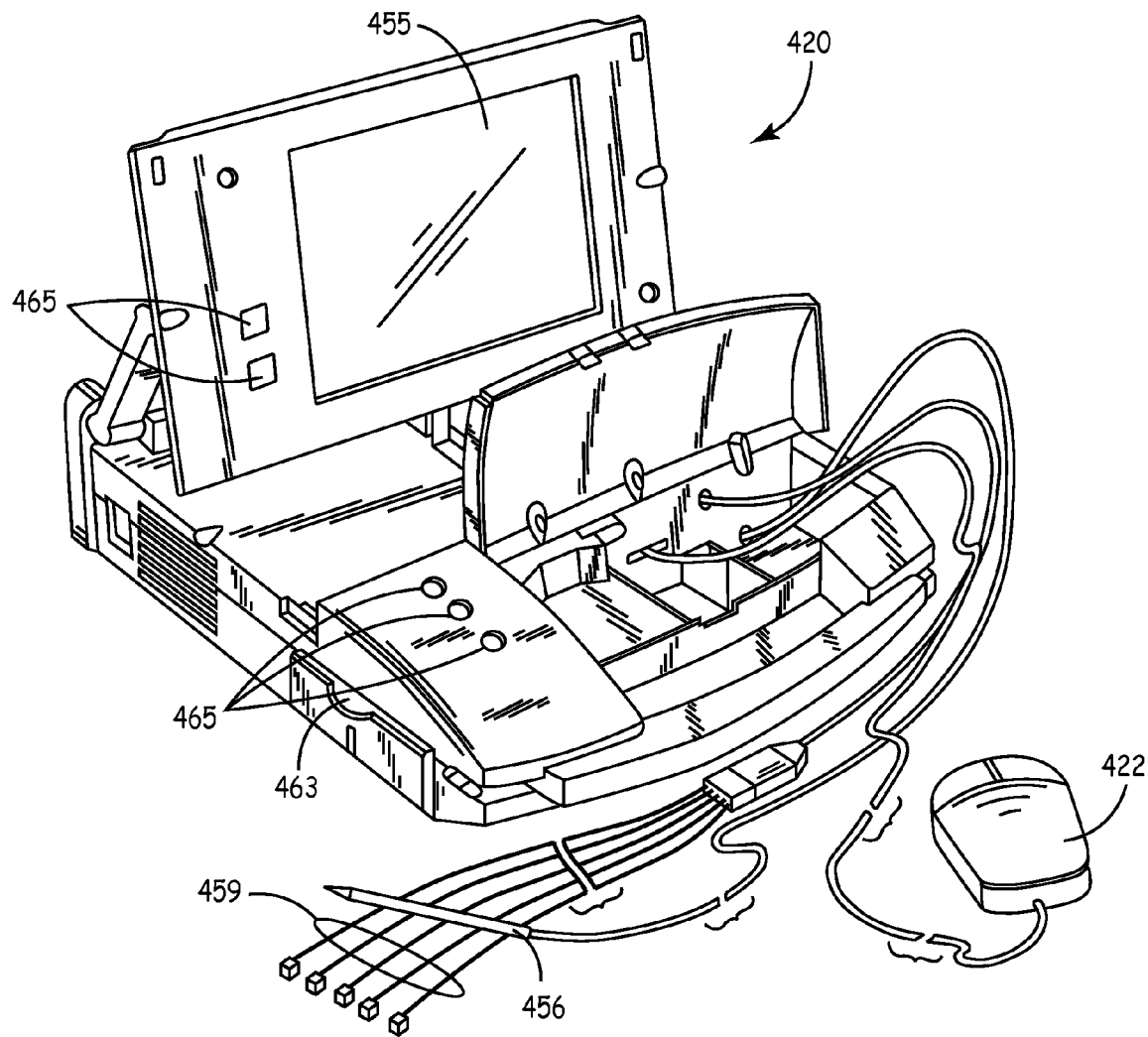
FIG. 4 is a functional schematic of the programmer of FIG. 3.

FIG. 4 is a functional schematic of the programmer of FIG. 3. As illustrated in FIG. 4, programmer 420 is a personal computer type, microprocessor-based device incorporating a central processing unit 450, which may be, for example, an Intel 80386 or 80486 or Pentium microprocessor or the like. A system bus 451 interconnects CPU 450 with a hard disk drive 452 storing operational programs and data, and with a graphics circuit 453 and an interface controller module 454. A floppy disk drive 466 or a CD ROM drive is also coupled to bus 451 and is accessible via a disk insertion slot within the housing of the programmer 420. Programmer 420 further includes an interface module 457, which includes digital circuit 458, non-isolated analog circuit 459, and isolated analog circuit 460. Digital circuit 448 enables interface module 457 to communicate with interface controller module 454.

In order for the physician or other caregiver or user to communicate with the programmer 420, control buttons 465 or optionally a keyboard coupled to CPU 50 are provided. However the primary communication mode is through graphics display screen 455 of the well-known "touch sensitive" type controlled by graphics circuit 453. A user of programmer 420 may interact therewith through the use of a stylus 456, also coupled to graphics circuit 453, which is used to point to various locations on screen 455, which display menu choices for selection by the user or an alphanumeric keyboard for entering text or numbers and other symbols.

Graphics display 455 also displays a variety of screens of telemetered out data or real time data including measurements of heart rate variability and heart rate trends according to the present invention. Programmer 420 is also provided with a strip chart printer 463 or the like coupled to interface controller module 454 so that a hard copy of a patient's ECG, EGM, marker channel or of graphics displayed on the display 455 can be generated.

As will be appreciated by those of ordinary skill in the art, it is often desirable to provide a means for programmer 420 to adapt its mode of operation depending upon the type or generation of implanted medical device to be programmed. Accordingly, it may be desirable to have an expansion cartridge containing EPROMs or the like for storing software programs to control programmer 420 to operate in a particular manner corresponding to a given type or generation of implantable medical device. In addition, in accordance with the present invention, it is desirable to provide the capability through the expansion cartridge or through the floppy disk drive 66 or CD ROM drive.

The non-isolated analog circuit 459 of interface module 457 is coupled to a programming head 422 which is used to establish the uplink and downlink telemetry links between the pacemaker 410 and programmer 420 as described above. Uplink telemetered EGM signals are received in programming head 422 and provided to non-isolated analog circuit 459. Non-isolated analog circuit 459, in turn, converts the digitized EGM signals to analog EGM signals and presents these signals on output lines A EGM OUT and V EGM OUT. These output lines may then be applied to a strip-chart recorder 463 to provide a hard-copy printout of the A EGM or V EGM for viewing by the physician. Similarly, the markers be received by programming head 422 are presented on the MARKER CHANNEL output line from non-isolated analog circuit 459.

Isolated analog circuit 460 in interface module 547 is provided to receive external ECG and electrophysiologic (EP) stimulation pulse signals. In particular, analog circuit 460 receives ECG signals from patient skin electrodes 459 and processes these signals before providing them to the remainder of the programmer system in a manner well known in the art. Circuit 460 further operates to receive the EP stimulation pulses from an external EP stimulator for the purposes of non-invasive EP studies, as is also known in the art.

In order to ensure proper positioning of programming head 422 over the antenna of the associated implanted device, feedback is provided to the physician that the programming head 422 is in satisfactory communication with and is receiving sufficiently strong RF signals. This feedback may be provided, for example, by means of a head position indicator, e.g. a light-emitting diode (LED) or the like that is lighted to indicate a stable telemetry channel.

Figure 5:
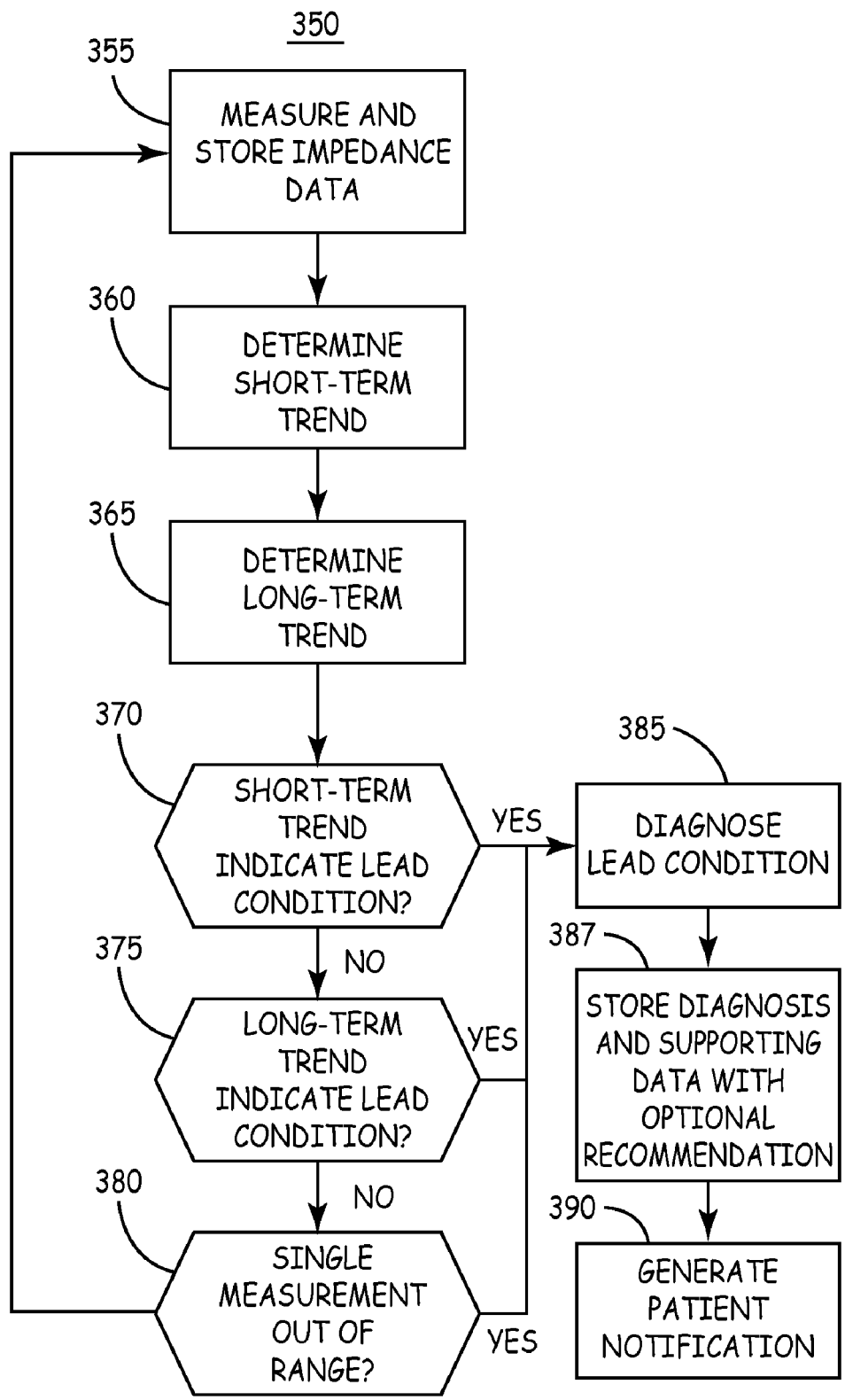
FIG. 5 is a flow chart of monitoring impedance trends for the detection and diagnosis of lead-related conditions according to an embodiment of the present invention.

FIG. 5 is a flow chart of monitoring impedance trends for the detection and diagnosis of a lead-related condition according to an embodiment of the present invention. The method 350 requires the measurement and storage of lead impedances at Block 355. Lead impedance measurements may be made on a periodic basis, preferably at least daily. Multiple periodic impedance measurements may be made depending on the number of leads present and the number of electrodes and conductors carried by each lead. For the configuration shown in FIG. 1, a preferred set of lead impedance measurements includes a low voltage pacing impedance measured across tip electrode 26 and ring electrode 24 and high voltage impedances measured across: 1) ring electrode 24 and can 11, 2) ring electrode 24 and coil electrode 20, 3) tip electrode 26 and coil electrode 20, and 4) tip electrode 26 and can 11.

Based on measured and stored lead impedances, relatively short-term impedance trend parameters are determined at Block 360, and relatively long-term impedance trend parameters are determined at Block 365. These short- and long-term impedance trend parameters are examined at decision Block 370 and 375 to determine if the trends are indicative of a lead-related condition. This examination may include comparing a periodic impedance measurement to impedance trend parameters to determine if diagnostic criteria for detecting a lead-related condition are met. If any of the examined trends are indicative of a lead condition, the condition is diagnosed at Block 385 based on the trend analysis. The diagnosed condition and supporting data may be stored in memory 226 at Block 387 so that a clinician may upload this information to an external device for review. A corrective action may optionally be recommended which may be to check for a loose connection between a lead and the associated IMD or replace a lead or add an additional lead while continuing to use the functioning part of the old lead. At optional Block 390, patient notification signal may be generated so that the patient is aware of a potential problem and seeks medical attention.

As a safety check in case of a sudden lead failure, a most recent lead impedance measurement may be compared to an acceptable range at decision Block 380. An acceptable range may be a predefined range of impedances known to be normal for a particular lead type. If a single measurement is out of the acceptable range, a lead-related condition is diagnosed at Block 385. If no trend or single impedance measurement indicate a lead-related condition as determined at decision Block 370, 375 and 380, the method 350 may operate in a looping fashion by returning to Block 355 to continue measuring and storing impedance data and updating the short-term and long-term impedance trends at Blocks 360 and 365.

Periodic impedance measurements are performed by impedance measurement circuit 204 under the control of microprocessor 224 and are stored in memory 226 of ICD 10. In one embodiment, impedance measurement data may be uplinked to an external device for analysis. Such data storage and transmission is provided in commercially available devices, for example in the GEM® Implantable Cardioverter Defibrillator available from Medtronic, Inc., Minneapolis, Minn. Determination and analysis of impedance trend parameters for detecting a lead-related condition may then be performed by an external device, which may be a programmer or personal computer. Uplinked impedance data may be alternatively be transferred via Internet to a central computer for analysis at a remote location. Reference is made to U.S. Pat. Appln. No. 20010031997 entitled "Instrumentation and software for remote monitoring and programming of implantable medical devices (IMDs)" to Lee, and U.S. Pat. Appln. No. 20010037366 entitled "System and method for providing remote expert communications and video capabilities for use during a medical procedure" to Webb et al., both patent applications being incorporated herein by reference in their entirety. Alternatively, impedance trend parameters may be determined by programs executed by microprocessor 224 and stored in memory 226. Subsequent analysis of impedance trends may be performed by microprocessor 224 or by an external device after uplinking a history of impedance measurements and impedance trend parameters from ICD 10. Preferably, the operations shown in FIG. 5 are performed in real-time by ICD 10 such that a lead-related condition may be detected early on and patient notification signal may be generated to alert the patient to seek medical attention. The detected lead-related condition and supporting data may then be uplinked to an external device for review by a physician, who may then take prompt action to confirm and correct the problem.

The operations summarized in FIG. 5 are shown in greater detail in the flow charts of FIGS. 6 through 9. FIG. 6A is a flow chart of a method for determining short-term and long-term impedance trend parameters that may be included in an embodiment of the impedance trend monitoring of FIG. 5. According to an embodiment of the present invention, impedance measurements are made at least daily and each daily impedance measurement is stored in memory 226 at Block 405. A given number of daily (or otherwise periodic) impedance measurements may be stored for a pre-determined term, for example the most recent 14 daily impedance measurements may be stored as short-term impedance measurements for determining a relatively short-term impedance trend.

A relatively longer term is defined for determining long-term impedance trends. According to an embodiment of the present invention, a long-term trend stores weekly measurements over many weeks, such as 1 year for example, or longer. The maximum impedance measurement measured over the relatively longer term and the minimum impedance measurement measured over the relatively longer term are preferably determined as the long-term maximum and long-term minimum impedances. In the method 400 of FIG. 6A, a weekly maximum impedance is determined and stored at Block 410, and a weekly minimum impedance is determined and stored at Block 415.

From the stored daily (short-term) measurements and weekly (long-term) impedance parameters, short-term and long-term trends may be determined. For example, a short-term median impedance is determined at Block 420 from a predetermined number of recent, consecutive periodic measurements. In one embodiment, the median of 14 daily impedance measurements is determined, for example.

Figure 6A:
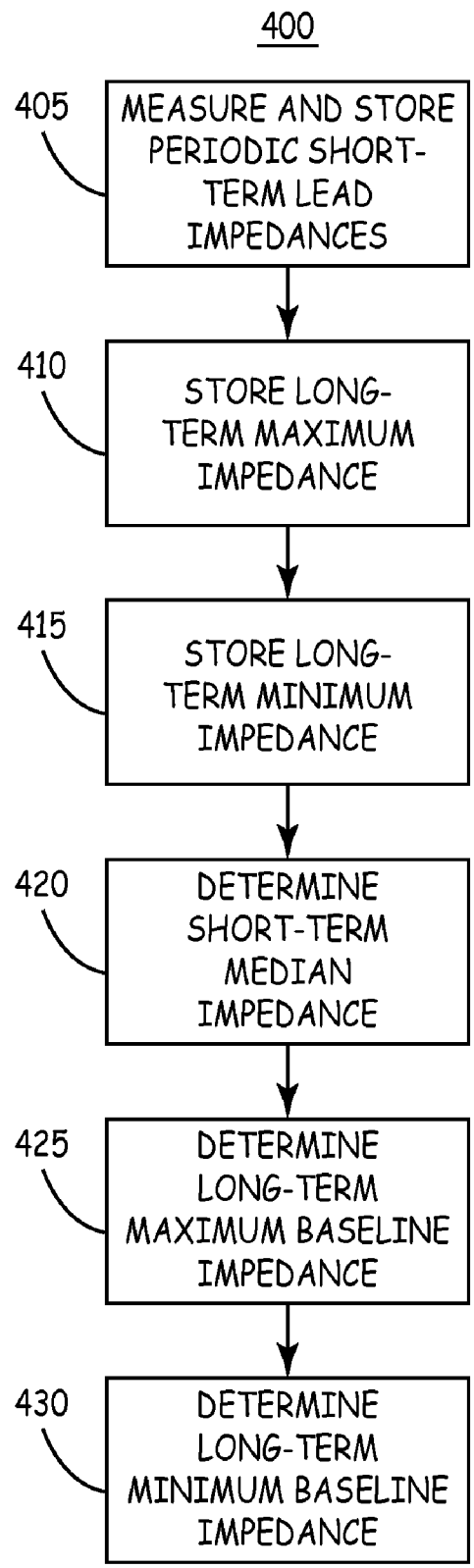
FIG. 6A is a flow chart of a method for determining short-term and long-term impedance trends that may be included in an embodiment of the impedance trend monitoring of FIG. 5.
Figure 6B:
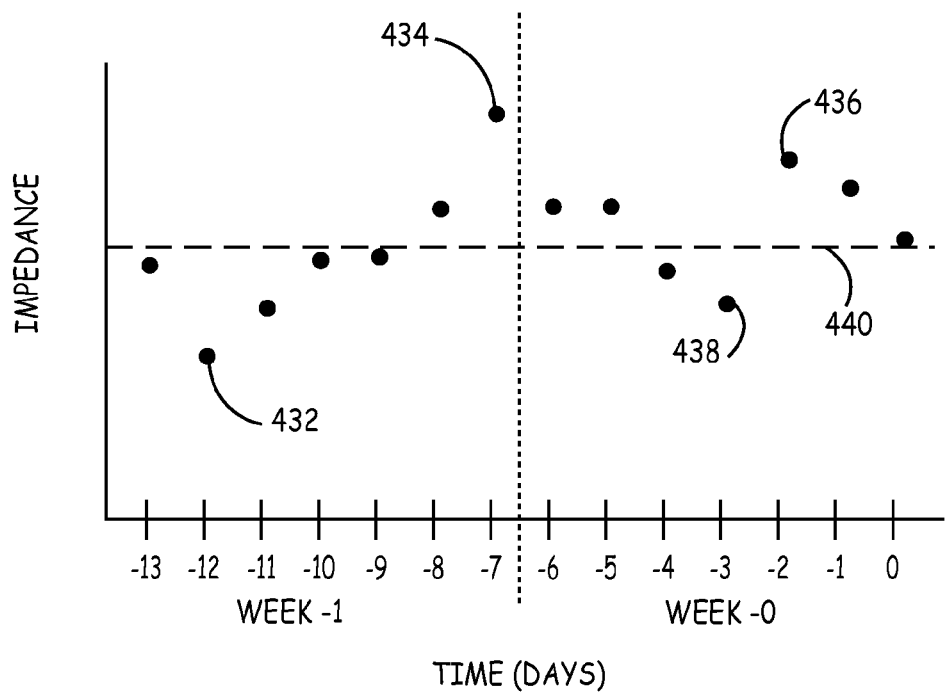
FIG. 6B is a graphical representation of hypothetical daily impedance data generated according to an embodiment of the present invention.

FIG. 6B is a graphical representation of hypothetical daily impedance data generated according to an embodiment of the present invention. As illustrated in FIGS. 6A and 6B, fourteen daily impedance measurements are plotted vs. time, from day 0 through 13 days prior, Block 405. The median daily impedance 440, indicated approximately by dashed line, is then determined in Block 420 from the 14 daily impedance measurements to monitor the trend of the measured short-term impedances. In addition, as described above, a weekly minimum impedance measurement and a weekly maximum impedance measurement is determined using the daily impedance data generated for each week and stored in memory 226. The highest impedance measurement 436 and the lowest impedance measurement 438 made during week 0 are stored as the weekly maximum and minimum impedance measurements, Blocks 410 and 415, respectively, for week 0. Likewise, the highest measurement 434 and lowest measurement 432 made during week −1 are stored as the weekly maximum and minimum impedances, Blocks 410 and 415, respectively, for week −1.

At Block 425 of FIG. 6A, a maximum baseline impedance is determined from stored long-term maximum impedance measurements, Block 410. Similarly, a minimum baseline impedance is determined, Block 430 from stored long-term minimum impedance measurements, Block 415. In one embodiment, trends of long-term maximum impedances and long-term minimum impedances are examined exclusively from each other. However, other algorithms could be designed that combine both maximum and minimum impedances. The maximum and minimum impedance measurements determined over a period of time may deviate significantly from a median measurement if a short or open has occurred along an impedance measurement pathway. For example, if a conductor fracture has occurred, a high impedance may be measured. The high impedance measurement may be intermittent, however, due to motion of the lead body. Periodic impedance measurements for the same pathway, therefore, may continue to fall in a normal range, or close to a median, with occasional high maximum impedance. Intermittent high long-term maximum impedances may therefore occur with a relatively stable minimum long-term impedance.

In another example, if a conductor insulation is breached, a low impedance measurement may occur. Again, a low impedance measurement may be intermittent due to lead movement resulting in some periodic impedance measurements to be relatively normal. Intermittent low long-term minimum impedances may occur with stable long-term maximum impedance. Thus, the trends in the weekly maximum and minimum impedances may be different and mutually exclusive, depending on the type of lead-related condition that may be present. In accordance with the present invention, therefore, a maximum weekly baseline and a minimum weekly baseline are determined to allow mutually exclusive analysis of trends in these parameters.

Figure 6C:
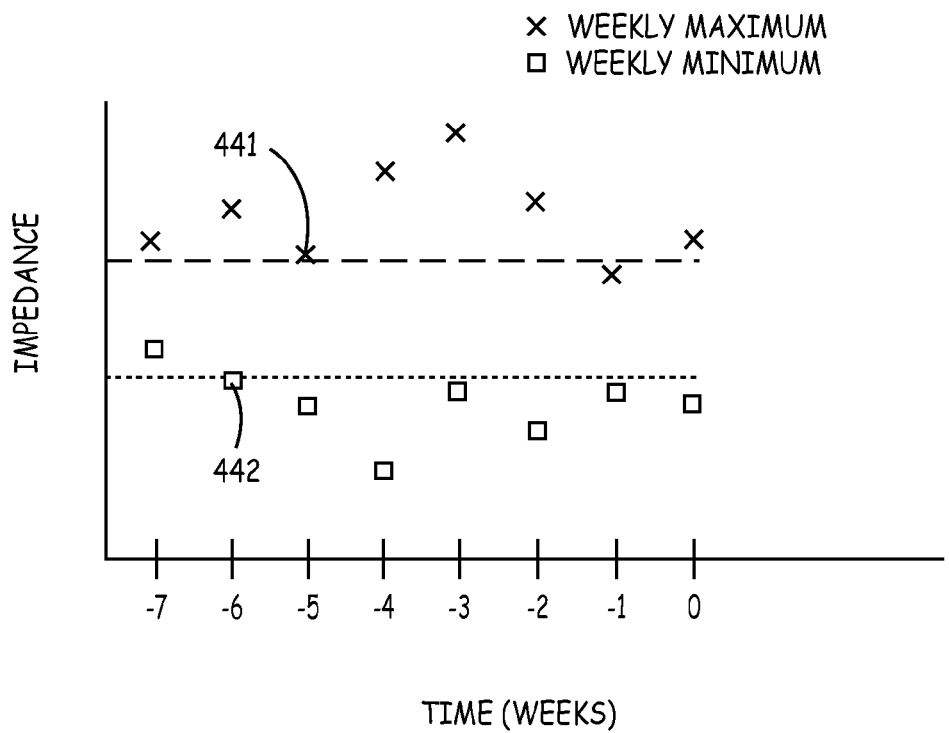
FIG. 6C is a graphical representation illustration of a method for determining long-term maximum and minimum baselines according to an embodiment of the present invention.

A long-term maximum baseline impedance, Block 425, and a long-term minimum baseline impedance, Block 430, may be determined based on the long-term maximum and minimum impedance measurements over a given number of terms. FIG. 6C is a graphical representation of a method for determining long-term maximum and minimum baselines according to an embodiment of the present invention. As illustrated in FIG. 6C, 8 weeks of maximum and minimum weekly impedance values, for example, are plotted vs. time, from week 0 through 7 weeks prior, although any number of weeks may be utilized. A long-term maximum baseline impedance 441 is determined as the second lowest weekly maximum impedance determined from the 8 weekly maximum impedance measurements. A long-term minimum baseline 442 is determined as the second highest weekly minimum impedance determined from 8 weekly minimum impedance measurements. By using the second lowest and second highest maximum or minimum impedance measurement for setting a maximum or minimum baseline, respectively, outliers may be ignored. Long-term maximum and minimum baseline impedances may alternatively be determined based on a median value of the maximum or minimum measurements, respectively, a percentage of a median value, or other function of the long-term maximum and minimum impedances. A new baseline is created each week using the most recent eight weeks, forming a sliding baseline window.

Other impedance trend parameters may be alternatively or additionally be determined such as impedance variability, slopes of short-term or long-term impedance measurements versus time, etc. Once parameters representing the short-term and long-term impedance trends have been obtained, subsequent periodic impedance measurements may be compared to these trend parameters to determine if a lead-related condition is present. Thus, method 400 of FIG. 6 may continue to method 450 of FIG. 7.

Figure 7:
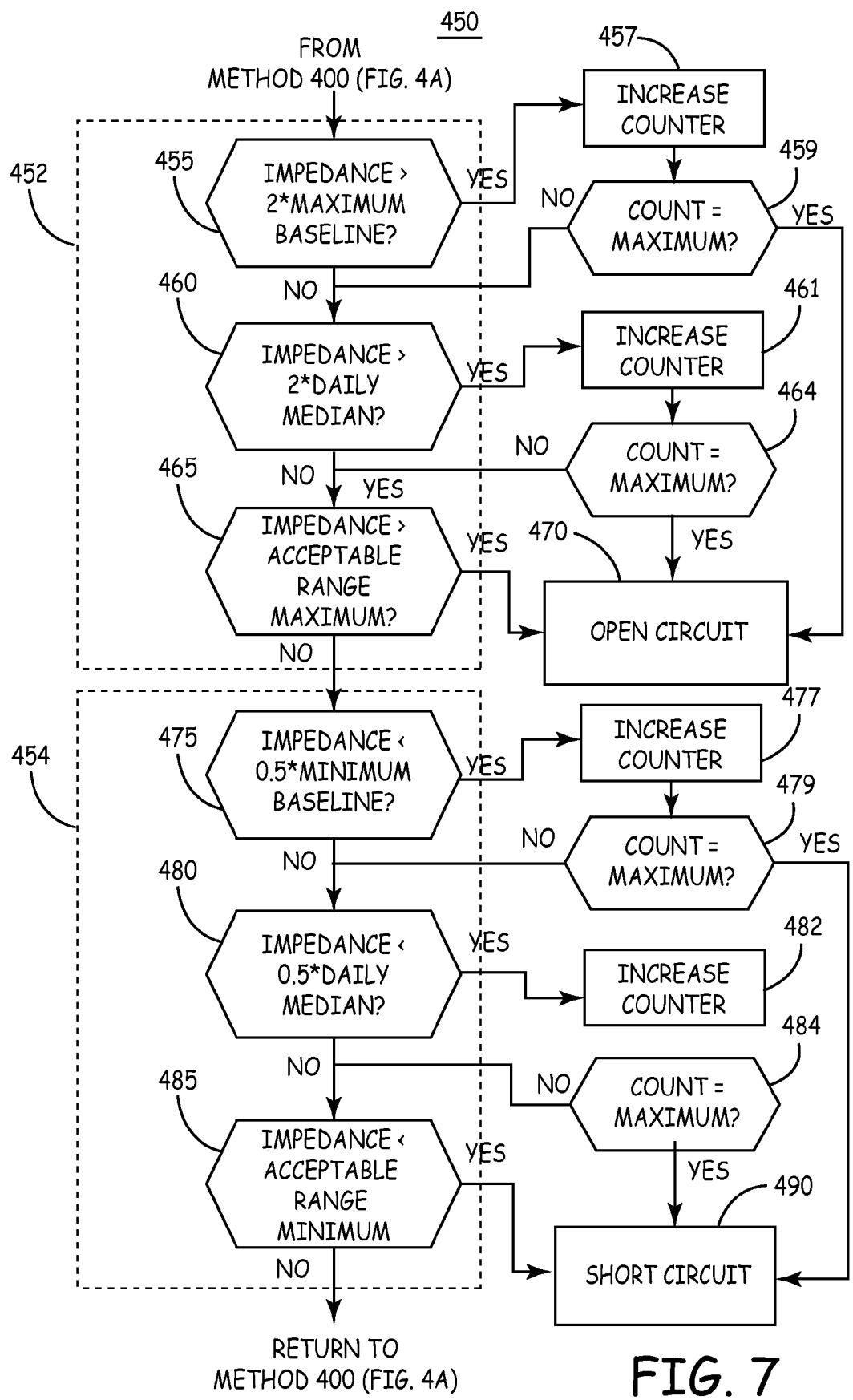
FIG. 7 is a flow chart illustrating a method of monitoring impedance to detect an open or short circuit according to an embodiment of the present invention.

FIG. 7 is a flow chart of a method of monitoring impedance to detect an open or short circuit according to an embodiment of the present invention. As illustrated in FIG. 7, the decision Blocks 455, 460 and 465 are included in an analysis 452 for determining if an open circuit is indicated. At Block 455, a long-term periodic impedance measurement is compared to a long-term maximum baseline measurement. According to an embodiment of the present invention, each subsequent daily impedance measurement is compared to the median daily impedance Block 440 and each subsequent weekly maximum impedance measurement is compared to the weekly maximum baseline impedance, Block 441, determined according to the method 400 described above, so that subsequent daily measurements are compared to the daily median and subsequent weekly measurements are compared to the weekly baselines. If the current weekly maximum impedance measurement is significantly greater than the weekly maximum baseline, Block 441, for example 2 times greater, a counter that has been previously initialized to 0 (not shown) is increased by one count at Block 457. Once the counter reaches a predetermined maximum as determined at decision Block 459, an open circuit is detected at Block 470. In one embodiment, an open circuit is detected if three weekly maximum impedance measurements exceed twice the weekly maximum baseline.

If the periodic impedance measurement does not significantly exceed the long-term maximum baseline, or if the counter of Block 457 has not reached the predetermined maximum, the current short-term impedance measurement is compared to the short-term median impedance at decision Block 460. For example, according to the embodiment illustrated in FIG. 6B, a daily impedance measurement is compared to the median of the 14 most recent daily measurements. If the current short-term measurement is significantly greater than the short-term median, for example more than twice the short-term median, a counter that has been previously initialized to 0 (not shown) is increased by one at Block 461. Once the counter reaches a maximum, as determined at decision Block 464, an open circuit is detected at Block 470. In one embodiment, an open circuit is detected if three periodic short-term impedance measurements exceed twice the short-term median impedance.

If the periodic measurement does not significantly exceed the short-term median impedance, or if the counter of Block 464 has not reached the maximum, the periodic short-term measurement is compared to a maximum acceptable impedance, at Block 465, which may be a fixed, predetermined value or a programmable value selected based on the type of lead used. In one embodiment, an open circuit is detected at Block 470 if the daily pacing impedance measurement exceeds 2000 ohms.

Thus an open circuit may be detected based on a single impedance measurement being outside of a predetermined range associated with either a median daily impedance or a single daily impedance threshold, or, in accordance with the present invention, based on a short-term or long-term impedance trend. Diagnostic criteria set for detecting a lead-related condition based on comparisons between a periodic impedance measurement and short-term and long-term impedance parameters may be tailored to a particular lead type. For example, the difference between a periodic lead measurement and an impedance parameter trend and the number of periodic measurements deviating significantly from an impedance parameter trend may be uniquely defined depending on the type of lead being monitored. Upon detection of an open circuit, the method 350 of FIG. 5 will store the lead-related condition along with the supporting data that led to the detection (Block 385) and may provide a recommended corrective action or generate a patient notification signal.

If an open circuit is not detected during the open circuit analysis, Block 452, the method 450 proceeds to Block 475 to begin an analysis 454 for detecting a short circuit, which includes the decision Blocks 475, 480 and 485. At Block 475, a long-term periodic impedance measurement is compared to a long-term minimum baseline measurement. According to an embodiment of the present invention, a subsequent weekly minimum impedance measurement is compared to the weekly minimum baseline impedance determined according to the method 400 described above. If the weekly minimum impedance measurement is significantly less than the weekly minimum baseline impedance, Block 475 for example less than half the weekly minimum baseline impedance, a counter, that has been previously initialized to 0 (not shown) is increased by one count at Block 477. Once the counter reaches a predetermined maximum as determined at decision Block 479, a short circuit is detected at Block 490. In one embodiment, a short circuit is detected if three daily impedance measurements are less than half the weekly minimum baseline.

If the periodic impedance measurement is not significantly less than the long-term minimum baseline, or the counter of Block 477 has not reached the maximum, the current short-term impedance measurement is compared to the short-term median impedance at decision Block 480. For example, according to the embodiment of FIG. 6B, a daily impedance measurement is compared to the median of the 14 most recent daily measurements. If the current short-term measurement is significantly less than the short-term median, for example less than half the short-term median, a counter that has been previously initialized to 0 (not shown) is increased by one at Block 482. Once the counter reaches a maximum, as determined at decision Block 484, a short circuit is detected at Block 490. In one embodiment, a short circuit is detected if three daily impedance measurements are less than half the short-term median impedance.

If the periodic measurement is not significantly less than the short-term median impedance, or if the counter of Block 484 has not reached the maximum, the periodic measurement is compared to a minimum acceptable impedance, which may be a fixed, predetermined value or a programmable value, at Block 485. In one embodiment, if the daily pacing impedance measurement is less than 200 ohms, an open circuit is detected at Block 490. Upon detection of a short circuit, method 350 of FIG. 5 will store the diagnosis and supporting data (Block 385) in memory 226 an optionally provide a recommended corrective action or generate a patient notification signal.

If an open or short circuit is not detected by method 450 of FIG. 7, the method 450 returns to Block 400 of FIG. 6A to collect the next periodic impedance measurement, update the trend parameters accordingly, and continue to test for a lead-related condition in a looping fashion. Tests for a lead-related condition may further include a more rigorous analysis of long-term trends to detect a gradually occurring condition.

Figure 8A:
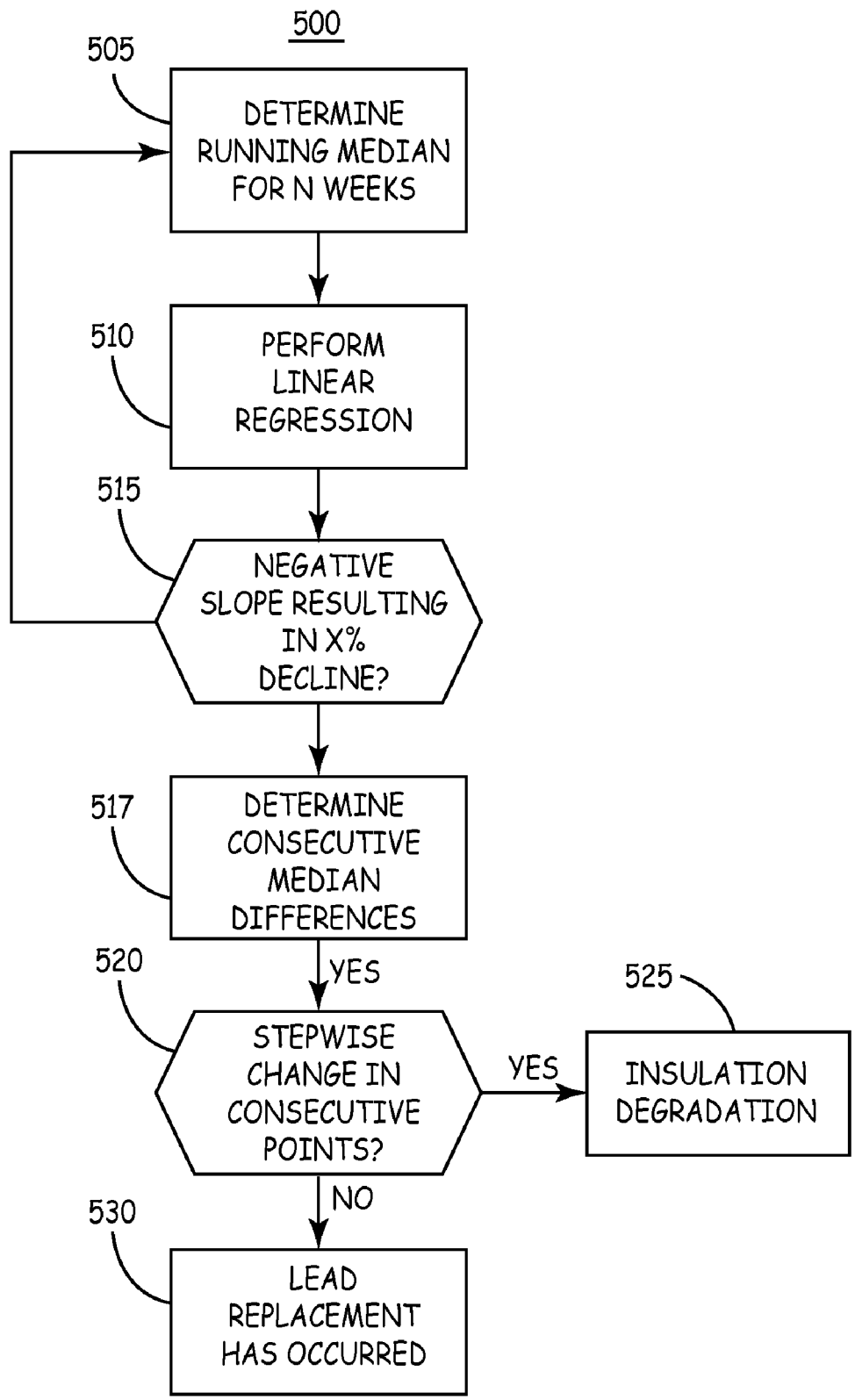
FIG. 8A is a flow chart of a method of monitoring impedance to detected insulation degradation according to an embodiment of the present invention.

FIG. 8A is a flow chart of a method of monitoring impedance to detect insulation degradation according to an embodiment of the present invention. According to the present invention, a gradual degradation of the outer insulation of a lead body may be detected by monitoring impedance trends over a relatively long-term. Method 500 begins at Block 505 by determining the running median of a given number of consecutive long-term minimum impedance measurements. In one embodiment, the median is determined from 5 weekly minimum impedance measurements. The running long-term median is then determined for a given number of terms. For example, a five-week median may be determined for 12 weeks. Next, parameteric linear regression is performed on the 12 five-week median values at Block 510. The slope of the linear regression, which may be a least squares fit, is then compared to a minimum acceptable slope at decision Block 515. If a negative slope is found that represents a decrease in the impedance over the 12-week period of greater than a predetermined percentage, X, for example 30%, then a lead degradation problem is suspected. If the comparison made at decision Block 515 is not affirmed, the method 500 returns to Block 505 to continue determining a running median of the weekly minimum impedance and performing the linear regression analysis at Block 510.

If the comparison at Block 515 is affirmed, then a decline in impedance due to a lead replacement must be excluded before concluding that lead degradation condition exists. A single "step-wise" decrease in lead impedance can occur when a lead has been replaced. Therefore, to verify that the overall decrease is not due to a step-wise decrease associated with a lead replacement, the difference between each of the consecutive five-week median values used in the parameteric analysis is determined at Block 517. If two consecutive medians differ by greater than a predetermined amount, for example greater than 35%, as determined at decision Block 520, then a lead replacement has occurred as concluded at Block 530. If consecutive median differences do not indicate a step-wise change, then the gradual decrease in the running median impedance is concluded to be due to insulation degradation at Block 525. This diagnosis and the supporting data are stored in memory 226 at Block 385 of method 350 (FIG. 5) for later uplinking to an external device for physician review, and a recommended action and/or a patient notification signal may be generated as described previously.

Figure 8B:
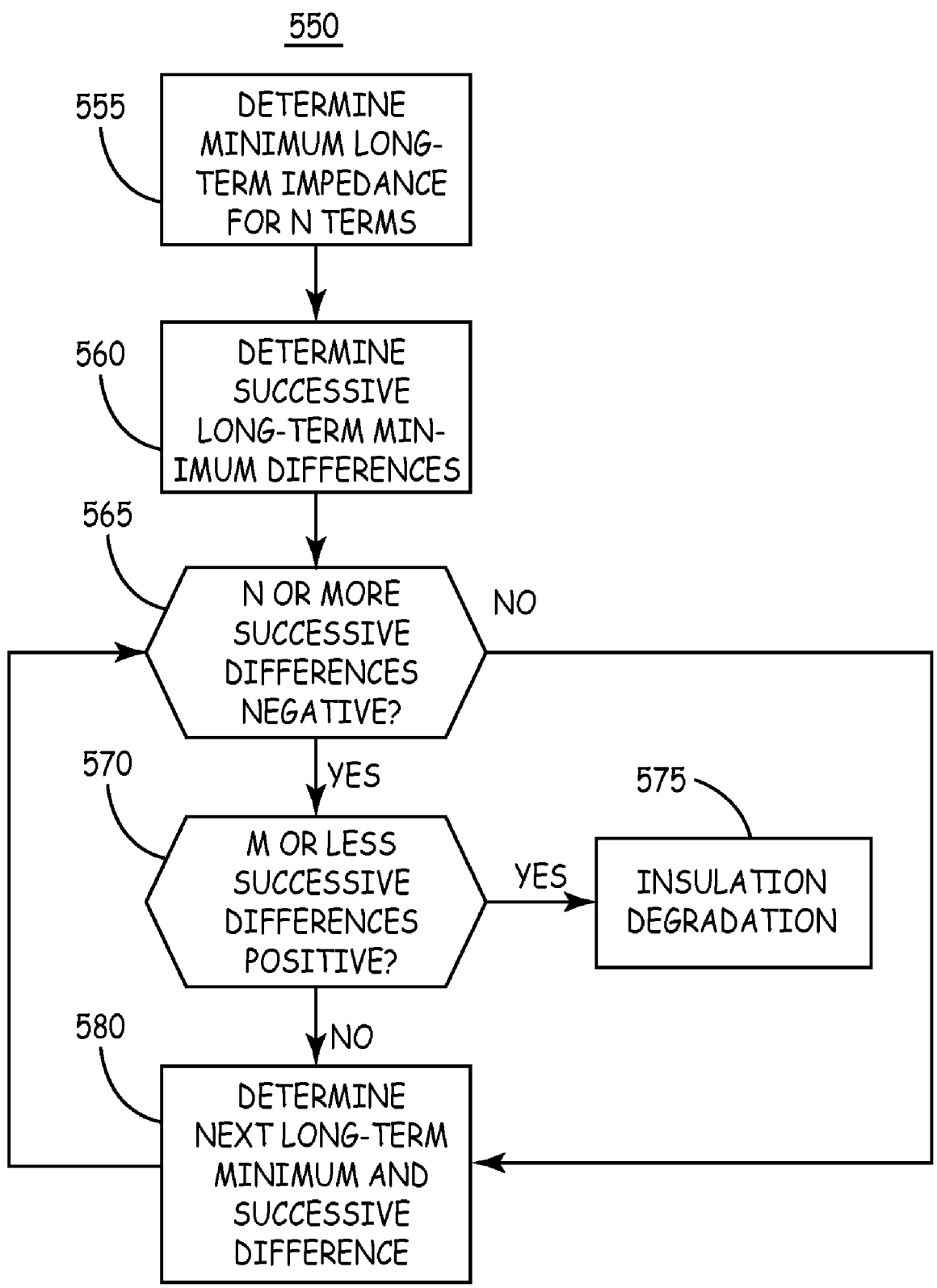
FIG. 8B is flow chart of a method for detecting lead insulation degradation using non-parameteric methods according to an embodiment of the present invention.

FIG. 8B is flow chart of a method for detecting lead insulation degradation using non-parameteric methods according to an embodiment of the present invention. In method 550, the long-term minimum impedance measurement is determined for a desired number of terms at Block 555. In a preferred embodiment, a weekly minimum impedance is determined for 12 weeks. At Block 560, the successive differences between the long-term minimum impedances are determined. At decision Blocks 565 and 570, a non-parameteric analysis is performed to determine if the successive differences indicate a gradually decreasing trend of the long-term minimum impedance. In one embodiment, a given number, N, successive differences must be negative with no more than a given number, M, successive differences being positive wherein N should be greater than M. In one embodiment, if successive differences between 12 weekly minimum impedance measurements have been determined, at least five successive differences must be negative, as determined at decision Block 565, and no more than two successive differences may be positive, as determined at Block 570, in order to diagnose a lead insulation degradation condition at Block 575. If the diagnostic requirements of the non-parameteric analysis are not met at decision Block 565 and 570, the next long-term minimum impedance and associated successive difference is determined at Block 580. Method 550 then returns to Block 565 to continue monitoring the successive differences to determine if the diagnostic requirements are met.

The method 450 of FIG. 7 for detecting an open or short circuit and methods 500 or 550 of FIGS. 8A and 8B for detecting insulation degradation represent general methods that may generally be applied to many lead types. Supplementary analyses of impedance trends may be performed for detecting lead-related conditions that are characteristic of a particular lead type.

One lead related condition that can occur with certain types of leads is degradation of a middle insulation layer due to metal ion oxidation. This type of degradation is observed in leads having coaxially arranged conductors separated by polyurethane insulation. This phenomenon is not observed in other types of leads, such as leads having conductors arranged in a multi-lumen, silicone rubber lead body. Therefore, supplementary analysis of impedance trend data may include an analysis for detecting and diagnosing metal ion oxidation induced degradation. In a preferred embodiment, the type of lead in which lead impedance measurements are being made is preferably known so that appropriate supplementary analyses may be made. The lead type may be entered manually as a lead model number upon implantation by the physician. If the lead type is not known, supplementary analyses preferably include tests that will exclude types of leads that would not be subject to the particular type of lead-related condition being investigated.

Figure 9:
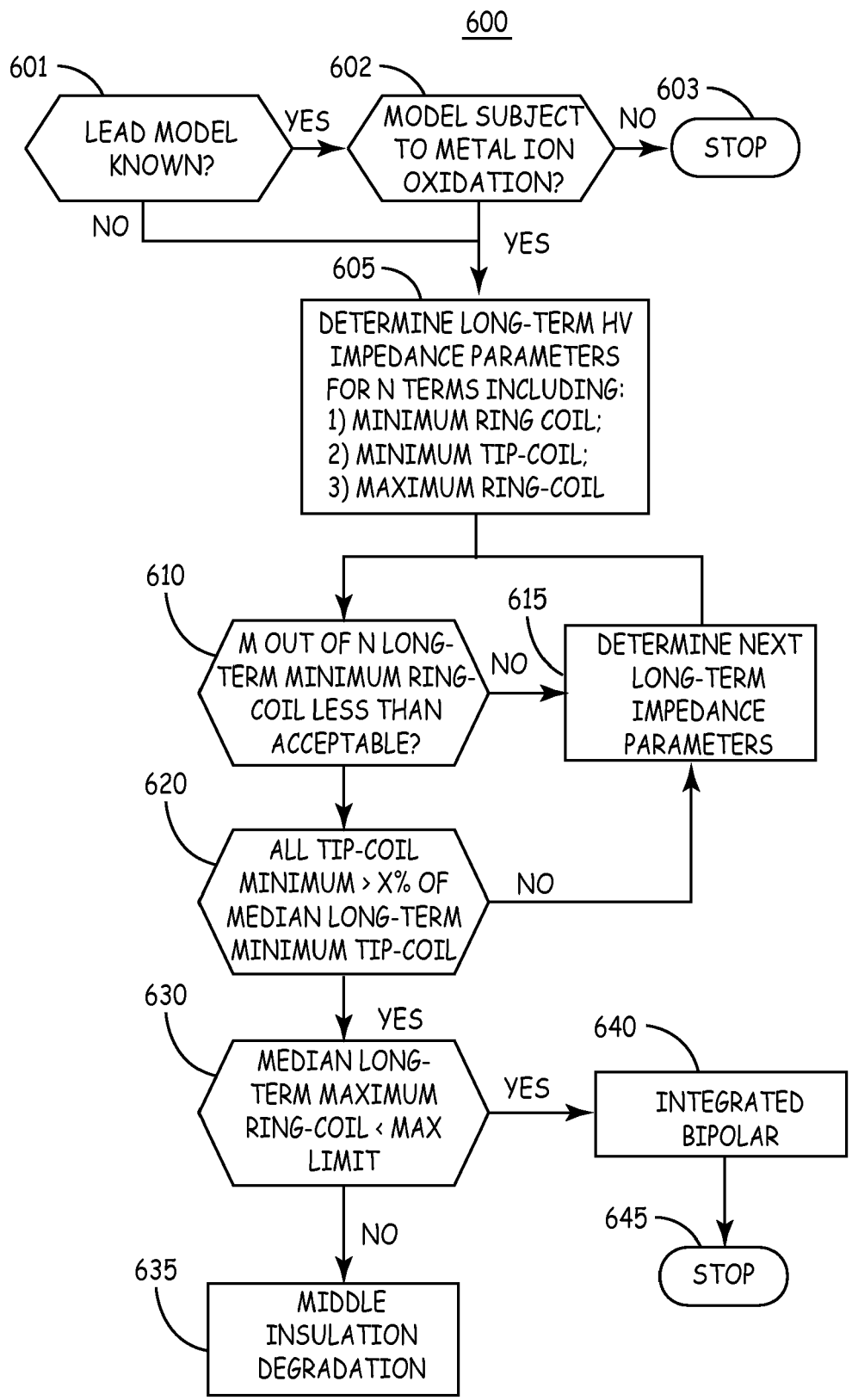
FIG. 9 is a flow chart of a method for monitoring trends in lead impedance parameters to detect middle insulation degradation due to metal ion oxidation according to an embodiment of the present invention.

FIG. 9 is a flow chart of a method for monitoring trends in lead impedance parameters to detect middle insulation degradation due to metal ion oxidation according to an embodiment of the present invention. Because this type of lead-related condition is specific to certain lead designs, method 600 begins at decision Block 601 to determine if the lead model in which lead impedance measurements are being made is known. If the lead model is not known, the method 600 may continue with the analyses but preferably includes steps for excluding leads not subject to metal ion oxidation (MIO) as will be described below.

If the lead model is known, method 600 determines if the model is subject to MIO at decision Block 602. The known lead model number may be compared to a list of lead model numbers known to be subject to MIO. If the lead model is not subject to MIO, method 600 is terminated at Block 603. If the lead is subject to MIO, method 600 continues to Block 605 to begin analyzing impedance trends.

In order to specifically diagnose middle insulation degradation, the trend of multiple lead impedance parameters is monitored. At Block 605 long-term impedance parameters are determined for multiple impedance measurement pathways. Middle insulation degradation due to MIO is typically observed in true bipolar defibrillation leads having polyurethane insulation between a coil electrode and a ring electrode. When this insulation layer begins to degrade, the impedance pathway along any pathway that includes the ring electrode and/or the coil electrode is affected. At Block 605, multiple long-term high-voltage (HV) impedance parameters are determined for a predetermined number of terms, N. The parameters preferably include a long-term minimum across ring and coil electrodes, a long-term minimum across the coil and can electrodes, and a long-term maximum across the ring and coil electrodes. In a preferred embodiment, the long term is a term of one week, and weekly parameters are collected for seven weeks.

At decision Blocks 610, 620 and 630, three criteria for diagnosing middle insulation degradation due to MIO are tested. The first criterion, tested at decision Block 610, is that a given number M, of the N long-term minimum ring-to-coil impedances must be less than an acceptable level, which would indicate a short between the ring and coil electrodes due to degradation of the intervening insulation. In a preferred embodiment, any four out of seven consecutive weekly minimum ring-to coil impedances must be lower than 14 ohms. If this criterion is not met, method 600 continues to Block 615 to determine the next long-term impedance parameters which will be stored in a rolling memory buffer designated for storing the most recent N parameters. After storing the new weekly parameters, the tests for MIO are repeated.

If the first criterion at decision Block 610 is satisfied, the second criterion is tested at decision Block 620. The second criterion is that each long-term minimum coil-can impedance is greater than a predetermined percentage of the median minimum coil-can impedance determined from the N terms. In a preferred embodiment, each weekly minimum coil-can impedance must be greater than 50% of the median of seven consecutive weekly minimum coil-can impedances. If any of the weekly minimum coil-can impedances is less than half of the median minimum coil-can impedance, then a short of the outer coil insulation may be present. An outer insulation problem will be detected and diagnosed by the methods described previously for detecting a short or general insulation degradation. When the second criterion is not met, the method 610 proceeds to Block 615 to determine the next long-term impedance parameters and will continue to monitor the impedance parameters according to the MIO diagnostic criteria.

If the second criterion is met, thereby ruling out that the decrease in the ring-coil minimum impedances found at decision Block 610 is not due to an outer insulation breach of the coil electrode, middle insulation degradation to MIO is likely to be present. The final criterion, tested at decision Block 630, is included in the case that the lead model number is not known. If the lead model number is not known, the lead in which impedances are being measured may be an integrated bipolar lead rather than a true bipolar lead. Middle insulation degradation due to MIO has not been observed in an integrated bipolar lead. Therefore, the third criterion is provided to establish that the lead is not an integrated bipolar lead.

The ring-coil impedances measured in an integrated bipolar lead will be considerably lower than the ring-coil impedances measured in a true bipolar lead. Therefore one way to discriminate between an integrated and true bipolar lead is to monitor the maximum long-term ring-coil impedance. If this maximum remains in a lower range, typical of an integrated bipolar lead, then the lead is known to be an integrated bipolar lead, generally not subject to MIO, rather than a true bipolar lead. Conversely, if the maximum long-term ring-coil impedance remains in a higher range, associated with a true bipolar lead, then the lead is known to be a true bipolar lead that is subject to MIO.

At decision Block 630, a median of a desired number of maximum long-term ring-coil impedances is compared to a predetermined maximum limit that is considered an upper boundary for the maximum ring-coil impedance of an integrated bipolar lead. In a preferred embodiment, the median of seven weekly maximum ring-coil impedances must be less than 5 ohms if the lead is an integrated bipolar lead. If this comparison is true, the lead is known to be an integrated bipolar lead as indicated at Block 640. No middle insulation condition is diagnosed.

If the comparison at decision Block 630 is not true, then the final criterion for diagnosing middle insulation degradation due to MIO in a true bipolar lead is satisfied as indicated at Block 635. This diagnosis and supporting data may be stored in memory 225 and a recommended corrective action, which would generally be lead replacement or addition of a ventricular pace/sense lead, may be indicated. A patient notification signal may be generated.

Thus, a lead-specific condition, such as middle insulation degradation due to MIO, may be diagnosed by monitoring multiple lead impedance measurement trends. This supplementary monitoring of impedance trends may be performed in addition to monitoring one or more individual lead impedance measurement trends for diagnosing general lead-related conditions associated with sudden or gradually occurring short or open circuits.

Figure 10:
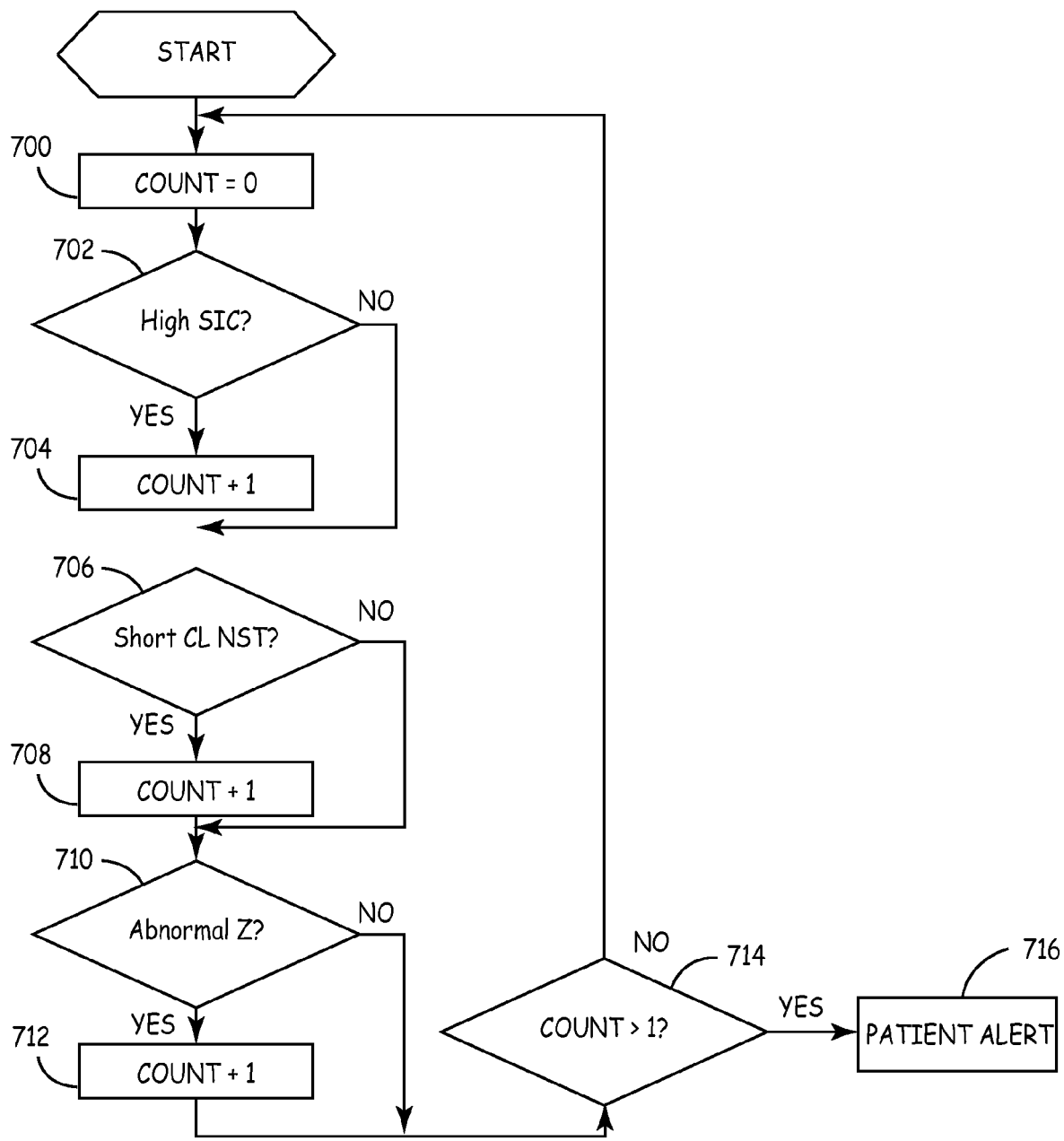
FIG. 10 is a flow chart of a method for detecting a lead-related condition according to an embodiment of the present invention.

FIG. 10 is a flow chart of a method for detecting a lead-related condiction according to an embodiment of the present invention. As illustrated in FIG. 10, once a method for detecting a lead-related condition is initiated, a criteria counter is set equal to zero, Block 700, and a determination is made as to whether a first oversensing criteria is satisfied, such as whether a sensing integrity counter has been satisfied, Block 702. If the first oversensing criteria is satisfied, as will be described below in detail, the criteria counter is incremented, Block 704. Once either the first oversensing criteria is determined to have been satisfied and the criteria counter has been incremented, or the first oversensing criteria is determined not to be satisfied, a determination is made as to whether a second oversensing criteria, such as a non-sustained event counter, is satisfied, Block 706. If the second oversensing criteria is satisfied, as will be described in detail below, the criteria counter is incremented, Block 708. Once either the second oversensing criteria is determined to have been satisfied and the criteria counter has been incremented, or the second oversensing criteria is determined not to be satisfied, a determination is made as to whether an impedance criteria determined using the methods described above is satisfied, Block 710. If the impedance criteria is satisfied, the criteria counter is incremented, Block 712. Once either the impedance criteria is determined to have been satisfied and the criteria counter has been incremented, or the impedance criteria is determined not to be satisfied, a determination is made as to whether more than one of the criteria has been met, Block 714.

If it is determined that more than one of the criteria have been met, such as both of the oversensing criteria or at least one of the oversensing criteria and the impedance criteria, a patient alert is triggered, Block 716. According to the present invention, the patient alert may be implemented in an implantable medical device implanted within the patient or may be implemented on a network server, as will be described below.

Figure 11:
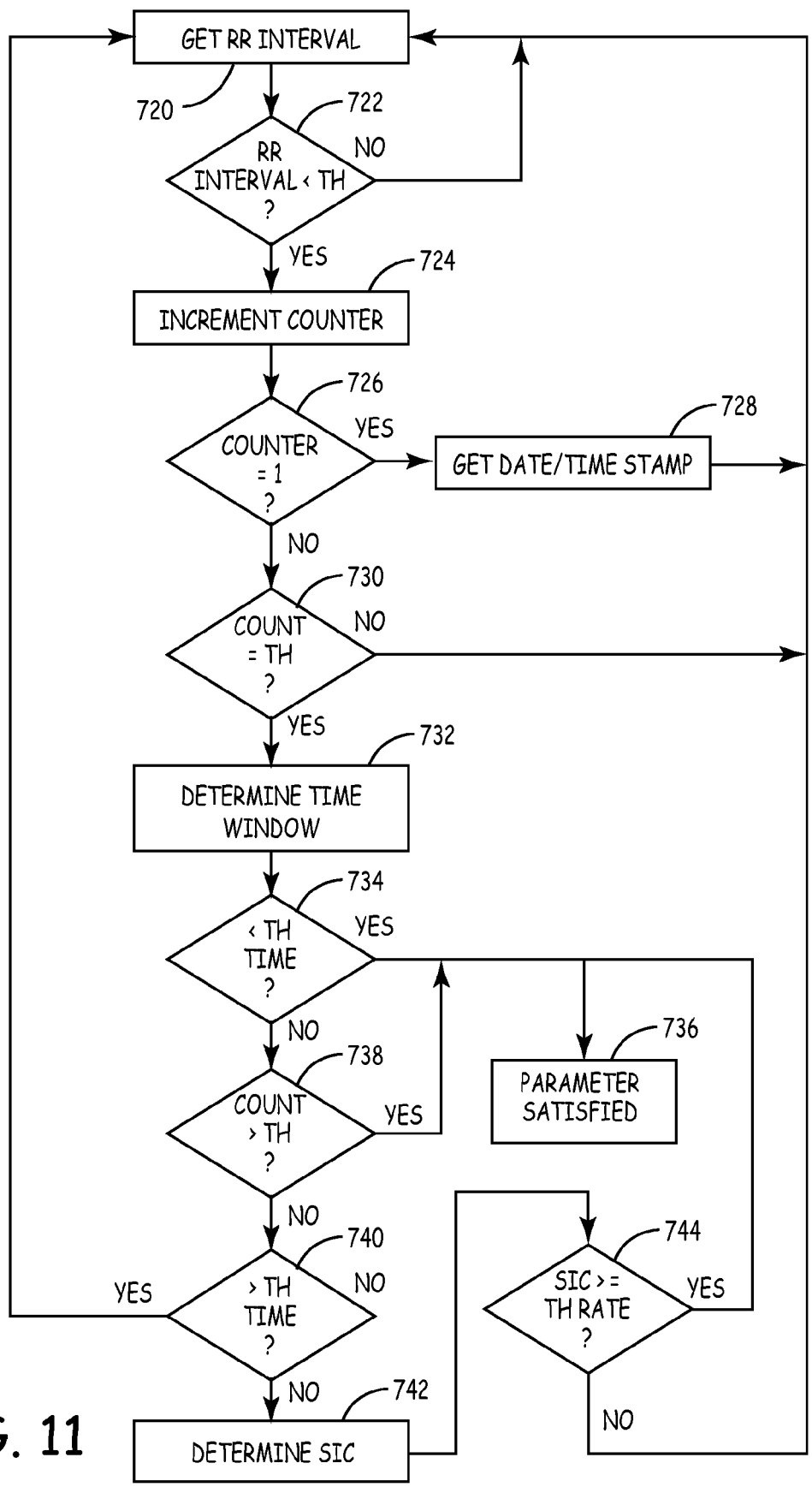
FIG. 11 is a flowchart of a method for determining whether an oversensing criteria has been satisfied according to an embodiment of the present invention.

FIG. 11 is a flowchart of a method for determining whether an oversensing criteria has been satisfied according to an embodiment of the present invention. As illustrated in FIG. 11, according to an embodiment of the present invention, in order to determine whether the sensing integrity counter has been satisfied in Block 702 in the method for detecting a lead-related condition of FIG. 10, a next RR-interval is determined, Block 720, and a determination is made as to whether the RR-interval is less than a predetermined threshold, Block 722. Since oversensing due to a lead related problem often occurs near the blanking period of the sense amplifier, the sensing integrity counter quantifies this oversensing by counting the number of RR-intervals that are determined to be less than a predetermined time period above the blanking period, such as 20 ms above the blanking period, for example. Since, in certain devices, the blanking period is set as 120 ms, the predetermined threshold of Block 722 would therefore be equal to approximately 140 ms, for example. According to an embodiment of the present invention, in devices in which the blanking period is programmable and can therefore have a value other than 120 ms, the predetermined threshold in Block 722 is simply set equal to the programmed blanking period plus 20 ms, with a maximum value of 170 ms, for example. While the predetermined time that the threshold is set above the blanking period is described as being 20 ms, it is understood that the present invention is not intended to be limited 20 ms, but rather, would include using any other desired time period.

If the RR-interval is not less than the predetermined threshold, and therefore is not near the blanking period, i.e., within 20 ms of the blanking period, a next RR-interval is obtained, Block 720, and a determination is made as to whether the next RR-interval is less than the predetermined threshold, Block 722. Each time that the current RR-interval is determined to be less than the predetermined threshold and therefore near the blanking period, a counter is incremented, Block 724. If the current RR-interval is the initial RR-interval determined to be near the blanking period for the current session, i.e., the counter is equal to one in Block 726, a date/time stamp since the last session is obtained from the timing and control circuitry 212, for example, to determine a start time of the current session, Block 728.

Once the session start time is determined, a next RR-interval is obtained, Block 720, and the process is repeated, with a determination being made as to whether the next RR-interval is less than the predetermined threshold, Block 722. If the current RR-interval is not the initial RR-interval determined to be near the blanking period for the current session, i.e., the counter is not equal to one in Block 726, a determination is made as to whether the number of RR-intervals that are near the blanking period, i.e., less than the threshold in Block 722, is equal to a predetermined threshold number, Block 730. If less than the predetermined threshold number of RR-intervals are near the blanking period, NO in Block 730, a next RR-interval is obtained, Block 720, and the process is repeated, with a determination being made as to whether the next RR-interval is less than the predetermined threshold, Block 722.

Once the number of RR-intervals that are near the blanking period is equal to the predetermined threshold number, YES in Block 730, a current time window duration is determined by taking the difference between the start time of the current session obtained in Block 728 and the current date/time stamp obtained from the timing and control circuitry 212, Block 732. Once the current time window duration is determined, a determination is made as whether the current time window duration is less than or equal to a threshold time window, Block 734. If the time duration window is less than or equal to the threshold time window, the oversensing criteria is determined to be satisfied, Block 736, and therefore the criteria counter, Block 704 of FIG. 10, is incremented.

According to an embodiment of the present invention, the predetermined threshold number utilized in Block 730 is set equal to thirty and the threshold time window is set equal to three days for Block 734, so that one way in which the oversensing criteria is satisfied and therefore the oversensing criteria counter is incremented is if thirty RR-intervals are determined to be near the blanking period within the first three days, for example. However, any desired values for the predetermined threshold number of Block 730 and the threshold time window of Block 734 without departing from the present invention. According to the present invention, the predetermined threshold number utilized in Block 730 is given a value corresponding to an indication that a mechanical problem associated with the lead is present, such as a loose set screw, and is therefore set equal to thirty, for example, although any desired value may be utilized. In addition, although three days is utilized in Block 734, any desired number of days or other time period may be utilized.

If the time duration window is greater than the threshold time window, NO in Block 734, a determination is made as to whether the number of RR-intervals determined to be near the blanking period during the current session is greater than a second predetermined threshold number, Block 738, by determining whether the counter in Block 724 is greater than the second predetermined threshold number of Block 738. According to an embodiment of the present invention, the second predetermined threshold number of Block 738 is set as 300, for example, although any threshold value may be chosen. If the number of RR-intervals near the blanking period is greater than the second threshold, the oversensing criteria is determined to be satisfied, Block 736, and the criteria counter, Block 704 of FIG. 10, is incremented. If the number of RR-intervals near the blanking period is less than or equal to the second threshold, No in Block 738, a determination is made as to whether the time duration window is greater than a second threshold time period, such as 30 days, for example, Block 740.

If the time duration window is not greater than the second threshold time period, an average sensing integrity counter per day is determined, Block 742, by dividing the count of the number of RR-intervals determined to be near the blanking period, Block 724, by the current time window duration determined in Block 732. A determination is then made as to whether the average sensing integrity counter per day is greater than or equal to a predetermined threshold rate, such as 10 per day, for example, Block 744, although the predetermined threshold rate in Block 744 could have any desired value associated with an indication of a lead-related condition. If the average sensing integrity counter per day is greater than or equal to the predetermined threshold rate, the oversensing criteria is determined to be satisfied, Block 736, and therefore the criteria counter, Block 704 of FIG. 10, is incremented. If average sensing integrity counter per day is not greater than or equal to the predetermined threshold rate, a next RR-interval is obtained, Block 720, and the process is repeated with a determination being made as to whether the next RR-interval is less than the predetermined threshold, Block 722.

Finally, if the number of RR-intervals near the blanking period is less than or equal to the second threshold, No in Block 738, and the time duration window is greater than the second threshold time period, YES in Block 740, a next RR-interval is obtained, Block 720, and the process is repeated with a determination being made as to whether the next RR-interval is less than the predetermined threshold, Block 722.

Figure 12:
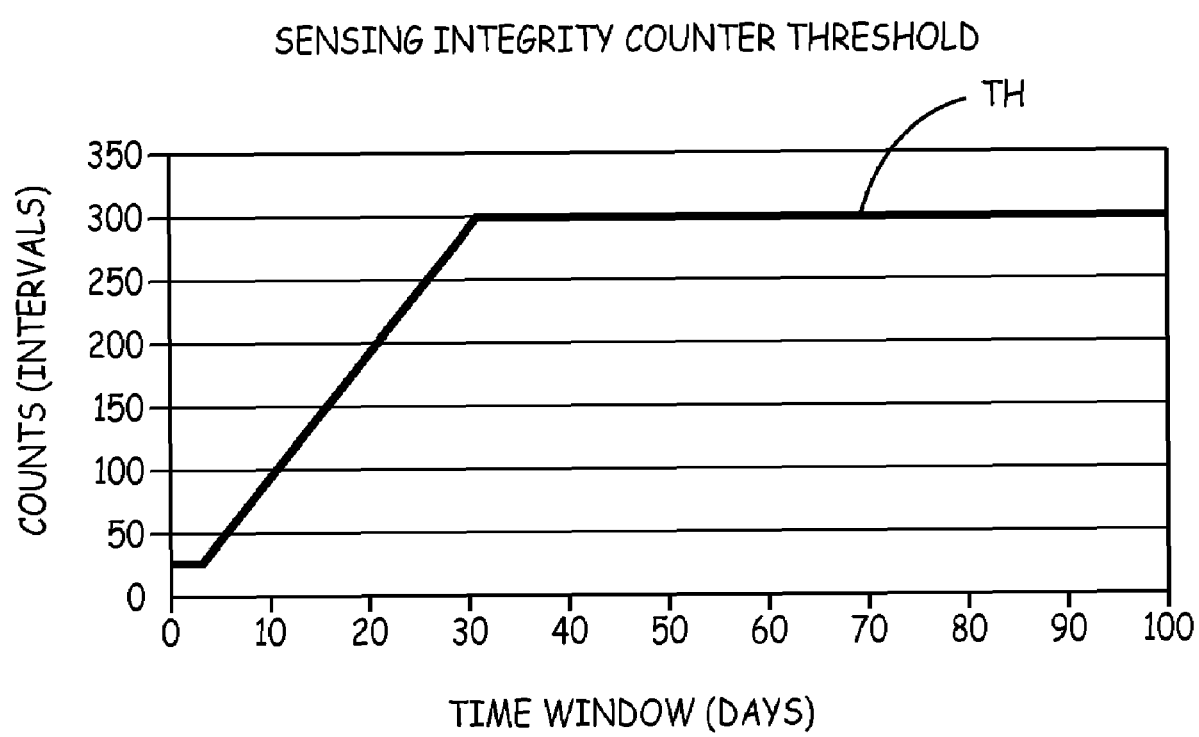
FIG. 12 is a graphical representation of a method for determining whether an oversensing criteria has been satisfied according to an embodiment of the present invention.

FIG. 12 is a graphical representation of a method for determining whether an oversensing criteria has been satisfied according to an embodiment of the present invention. In this way, as illustrated in FIG. 12, a threshold TH for determining when the sensing integrity criteria is satisfied and therefore the criteria counter of Block 704 of FIG. 10, is incremented, changes at predetermined time periods. In particular, for the first three days of the current session the threshold TH is satisfied once more than thirty RR-intervals are determined to be near the blanking period. Once three days have expired and there have not been thirty RR-intervals determined to be near the blanking period, the threshold is satisfied once there are determined to be an average of ten RR-intervals per day that are determined to be near the blanking period. After thirty days have expired in the current session, the threshold is satisfied once there have been a total of three hundred RR-intervals determined to be near the blanking period.

Figure 13:
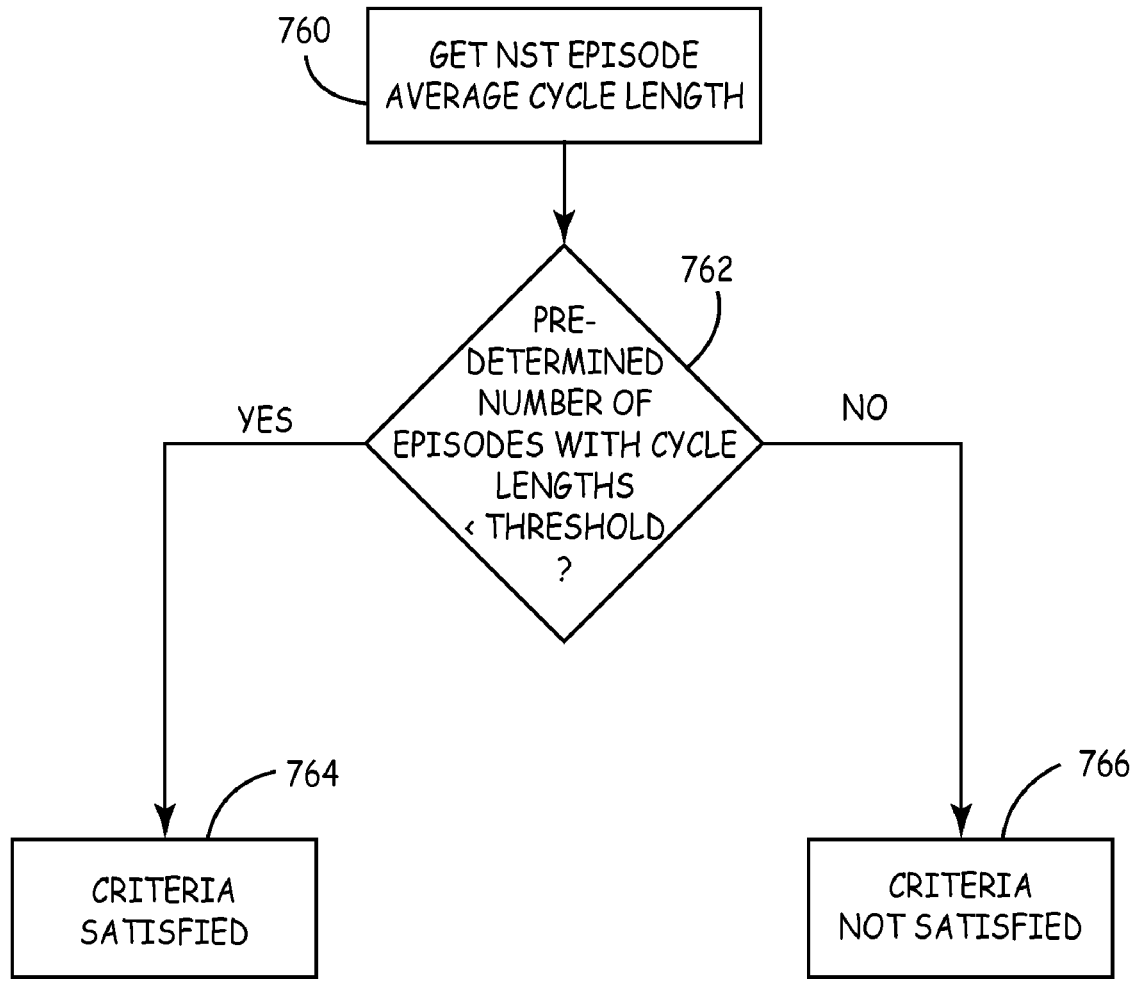
FIG. 13 is a flowchart of a method for determining whether an oversensing criteria has been satisfied according to an embodiment of the present invention.

FIG. 13 is a flowchart of a method for determining whether an oversensing criteria has been satisfied according to an embodiment of the present invention. As illustrated in FIG. 13, according to an embodiment of the present invention, a second oversensing criteria utilized in the method for detecting a lead related condition relates to identification of non-sustained episodes. During the normal detection process, the device detects ventricular tachyarrhythmias (VF, VT and FVT) by comparing time intervals between sensed events to a set of programmable detection intervals. For example, when the interval between sensed ventricular events is between 320 and 400 ms, a ventricular tachycardia (VT) interval counter is incremented. Once a certain number events associated with the VT interval are detected, such as 16 events, for example, a VT event is detected and the device responds appropriately.

In addition, a non-sustained ventricular tachycardia event is identified and stored within a non-sustained (NST) episode log when less than the required number of events associated with the VT interval are detected, i.e., less than 16 events, but more than a predetermined number of events associated with the VT interval are identified, such as five for example. The NST episode log stores information relating to the non-sustained events, including a date/time stamp and an average cycle length of each non-sustained episode. Because it has been determined that consecutive oversensed events may trigger storage of an inappropriate non-sustained episode in the NST episode log, the present invention utilizes the NST episode log as the second oversensing component in detecting a lead-related condition, as described above in reference to FIG. 10.

For example, as illustrated in FIG. 13, in order to determine whether the second sensing integrity counter has been satisfied in Block 706 of the method for detecting a lead-related condition of FIG. 10, the average cycle lengths for the non-sustained VT events stored in the NST episode log are obtained, Block 760, and a determination is made as to whether there are a predetermined number of non-sustained VT events having average cycle lengths that are less than a predetermined threshold occurring within a predetermined time frame, Block 762. For example, ventricular arrythmia episodes typically have an average cycle length greater than 200 ms and non-sustained episodes with average cycle lengths less than 200 ms are likely due to oversensing. Therefore, according to an embodiment of the present invention, a determination is made in Block 762 as to whether two non-sustained VT events having a cycle length less than 200 ms occur within a one week interval.

If the predetermined number of non-sustained VT events having average cycle lengths that are less than the predetermined threshold occur within the predetermined time frame, the second oversensing criteria is determined to be satisfied, Block 764, and therefore the criteria counter, Block 706 of FIG. 10, is incremented. If there are not the predetermined number of non-sustained VT events having average cycle lengths that are less than the predetermined threshold occurring within the predetermined time frame, the second oversensing criteria is determined not satisfied, Block 766, and the process of detecting a lead-related condition determines whether the other components are satisfied.

Figure 14:
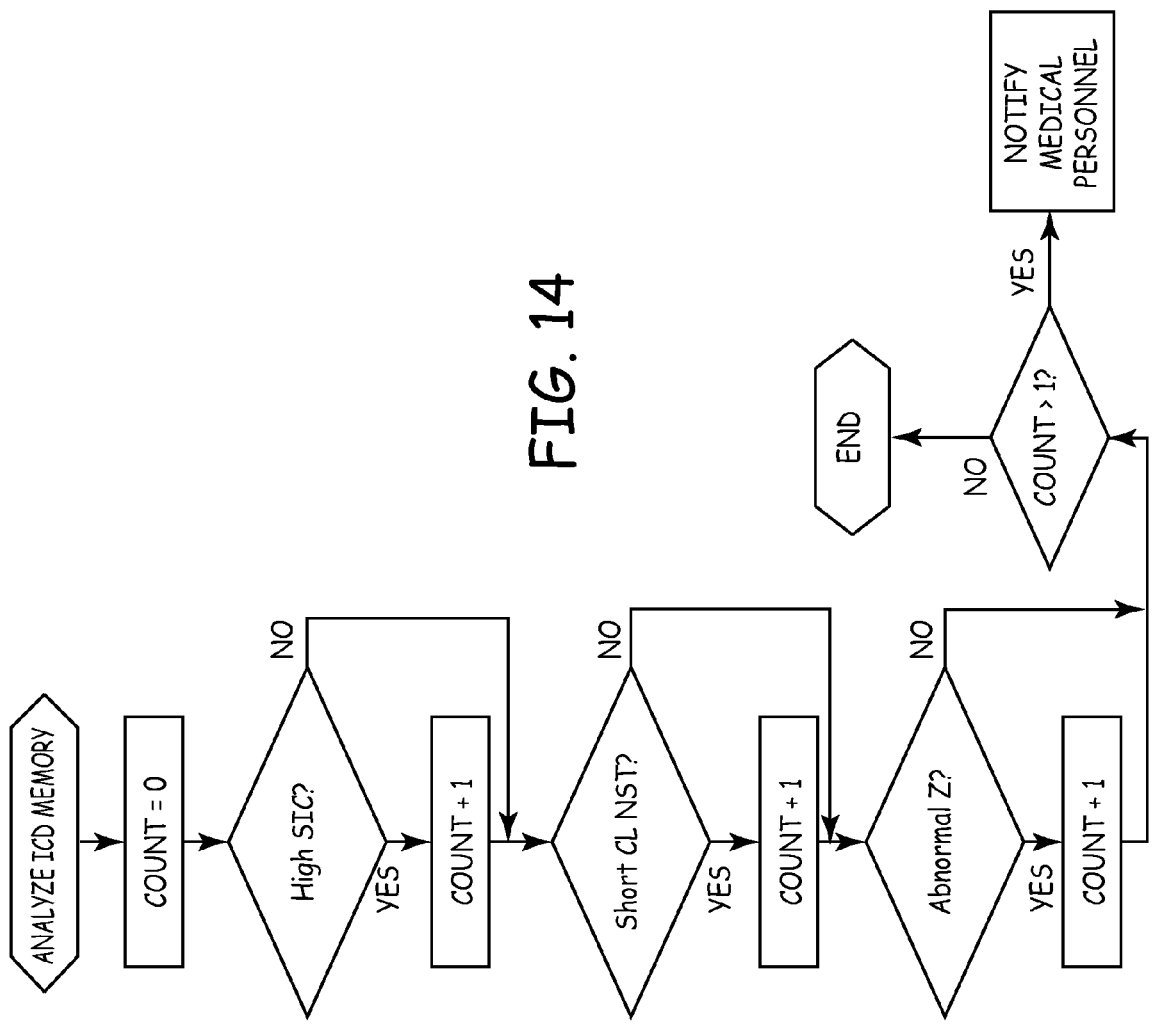
FIG. 14 is a flowchart of a method for detecting a lead-related condition according to an embodiment of the present invention.

FIG. 14 is a flowchart of a method for detecting a lead-related condition according to an embodiment of the present invention. As illustrated in FIG. 14, according to an embodiment of the present invention, the method for detecting a lead related condition is initiated either upon a visit to a medical facility by the patient, or in conjunction with a wireless download of the stored information from the implanted device remotely by the patient over a wireless network, Block 901. The stored information may be automatically transmitted using wireless telemetry to a receiver box located in the patients home that displays a message concerning a potential lead-related condition, and that sends information to the network and alerts medical personnel. Once the stored information related to the impedance trends and the oversensing measures are transmitted from the implanted device to a programmer during an office visit, or to a remote server or patient management network via telemetry circuit 330, the method for detecting a lead related condition is initiated and is performed outside the implanted device as described above. Blocks 900-914 of FIG. 14 for performing the method for detecting a lead related condition correspond to Blocks 700-714 of FIG. 10 and therefore detailed description of Blocks 900-914 of FIG. 14 are omitted merely for brevity sake.

Figure 14A:
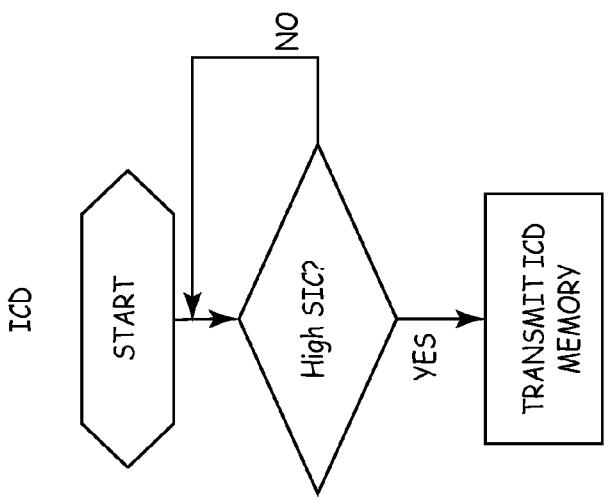
FIG. 14A is a flowchart of initiation of a method for detecting a lead-related condition according to an embodiment of the present invention.

As illustrated in FIG. 14, according to an embodiment of the present invention, once more than one of the three criteria have been met, YES in Block 914, medical personnel are notified either by an alarm or other indication associated with the programmer, or remotely via wireless telemetry. FIG. 14A is a flowchart of initiation of a method for detecting a lead-related condiction according to an embodiment of the present invention. As illustrated in FIG. 14A, according to an embodiment of the present invention, transmission of the stored information related to the impedance trends and the oversensing measures to a remote location may be initiated once one of the three criteria have been determined to be satisfied by the implanted device, such as once one of the oversensing criteria have been satisfied. In this way, once one of the three criteria (impedance trends, sensing integrity counter, and the non-sustained log) is determined to be satisfied by the implanted device, transmission of the stored information related to the impedance trends and the oversensing measures is initiated, Block 918. If a lead related condition is subsequently determined, an alert is transmitted to either the patient and/or medical personnel. As a result, by allowing the method for detecting a lead related condition to be performed external to the implanted device, updates to the method for determining a lead-related condition of the present invention may be implemented without having to replace or update software within the implanted device.

Some of the techniques described above may be embodied as a computer-readable medium that includes instructions for a programmable processor such as microprocessor 224 or pacer timing/control circuitry 212 shown in FIG. 2. The programmable processor may include one or more individual processors, which may act independently or in concert. A "computer-readable medium" includes but is not limited to any type of computer memory such as floppy disks, conventional hard disks, CD-ROMS, Flash ROMS, nonvolatile ROMS, RAM and a magnetic or optical storage medium. The medium may include instructions for causing a processor to perform any of the features described above for actively determining a coupling interval according to the present invention.

The detailed description of the embodiments of the present invention provided herein yield a sensitive and specific method for diagnosing lead-related conditions based on short-term and long-term impedance trends and two measures of oversensing. It will be apparent to those skilled in the art that numerous variations of the described embodiments are possible for practicing the invention. Therefore, the embodiments described herein should be considered exemplary, rather than limiting, with regard to the following claims.

What is claimed is:

1. An apparatus for determining a lead-related condition associated with an implantable medical device capable of being implanted in a patient, comprising:

a sensing device sensing intrinsic signals of the patient; and a processing unit determining, in response to the sensed intrinsic signals, whether more than one of a first oversensing criteria, a second oversensing criteria and an impedance criteria have been satisfied, wherein the processing unit determines the first oversensing criteria is satisfied in response to determining that a predetermined number of RR-intervals that are within a first predetermined time period subsequent to a blanking period associated with a sensing device occur within a second predetermined time period, wherein the processing unit determines the first oversensing criteria is satisfied in response to determining that the number of RR-intervals within the first predetermined time period is greater than a first predetermined threshold, and wherein the processing unit determines the first oversensing criteria is satisfied in response to determining that a time duration window is not greater than a threshold time period and determining that a ratio of RR-intervals within the first predetermined time period occur.

2. The apparatus of claim 1, further comprising a notification system generating an alert in response to the processor unit determining more than one of the first oversensing criteria, the second oversensing criteria and the impedance criteria have been satisfied.

3. The apparatus of claim 2, wherein the alert is transmitted to a remote location.

4. The apparatus of claim 1, wherein the first predetermined time period is approximately equal to 20 ms, the second predetermined time period is approximately equal to 72 hours and the predetermined number of RR-intervals is approximately equal to 30 RR-intervals.

5. The apparatus of claim 1, wherein the first predetermined time period is approximately equal to 20 ms and the first predetermined threshold is approximately equal to 300 RR-intervals.

6. The apparatus of claim 1, wherein the threshold time period is approximately equal to thirty days and the ratio of RR-intervals is greater than or equal to ten RR-intervals per day.

7. The apparatus of claim 1, wherein the processing unit determines the second oversensing criteria is satisfied in response to a predetermined number of events having average cycle lengths that are less than a second predetermined threshold occurring within a third predetermined time period.

8. The apparatus of claim 7, wherein the predetermined number of events is approximately equal to 2, the second predetermined threshold is approximately equal to 200 ms, and the third predetermined time period is approximately equal to one week.

9. The apparatus of claim 7, wherein the processing unit determines the impedance criteria has been satisfied in response to a set of diagnostic criteria being applied to a short-term lead-impedance trend and long-term impedance trend.

10. The apparatus of claim 9, further comprising:

a storage device storing information corresponding to the first oversensing criteria, the second oversensing criteria and the impedance criteria; and a transmitting device transmitting the stored information to a remote device, wherein the determination whether the first oversensing criteria, the second oversensing criteria and the impedance criteria is performed by the processing unit at the remote device.

11. The apparatus of claim 9, further comprising:

a storage device storing information corresponding to the first oversensing criteria, the second oversensing criteria and the impedance criteria in an implantable medical device;

a remote device remote from the implantable medical device;

a second processing unit positioned within the remote device; and a transmitting device transmitting the stored information to the remote device in response to the processing unit determining one of the first oversensing criteria, the second oversensing criteria and the impedance criteria is satisfied, wherein the second processing unit determines whether the other of the first oversensing criteria, the second oversensing criteria and the impedance criteria are satisfied.

* * * * *